US007887794B2

(12) United States Patent
Luquet et al.

(10) Patent No.: US 7,887,794 B2
(45) Date of Patent: Feb. 15, 2011

(54) LACTIC ACID BACTERIA AND THEIR USE IN THE TREATMENT OF CANCER

(75) Inventors: François-Marie Luquet, Orsay Paris (FR); Cindy Baldwin, Laval (CA); Monique Lacroix, Saint-Lambert (CA)

(73) Assignee: Bio-K Plus International, Inc., Laval, Quebec (CA)

( * ) Notice: Subject to any disclaimer, the term of this patent is extended or adjusted under 35 U.S.C. 154(b) by 0 days.

(21) Appl. No.: 10/496,924

(22) PCT Filed: Nov. 27, 2002

(86) PCT No.: PCT/CA02/01826

§ 371 (c)(1),
(2), (4) Date: Jan. 3, 2005

(87) PCT Pub. No.: WO03/045405

PCT Pub. Date: Jun. 5, 2003

(65) Prior Publication Data

US 2005/0208033 A1 Sep. 22, 2005

(30) Foreign Application Priority Data

Nov. 27, 2001 (CA) .................................. 2,364,249

(51) Int. Cl.
*C12N 1/20* (2006.01)
*A01N 63/00* (2006.01)
(52) U.S. Cl. .................................. 424/93.45; 435/252.9
(58) Field of Classification Search ............. 514/2; 424/93.45
See application file for complete search history.

(56) References Cited

FOREIGN PATENT DOCUMENTS

| WO | WO 98/23727 | * | 6/1998 |
| WO | WO98/23727 | * | 6/1998 |
| WO | WO 9823727 | | 6/1998 |

OTHER PUBLICATIONS

Rao et al (International J of Oncology, 1999, 14:939-944).*
Hague and Paraskeva (European J of Cancer Prevention, 1995, 4:359-364, IDS).*
Kailasapathy and Chin (Immunology and Call Biology, 2000, 78:80-88, IDS).*
Ardalan et al (Cancer Investigation, 1998, 16:237-251).*
Lankaputhra et al (Mutation Research, 1998, 397:169-182).*
Biasco et al (Ital J Gastroenterology, 1991, 23:142).*
Luquet (WO 98/23727, published Jun. 4, 1998).*
Leu et al (J. Nutr, 2005, 135:996-1001).*
Baricault et al (Carcinogenesis, 1995, 16:254-252, IDS).*
Kazuhiro Hirayama et al., "The Role of Probiotic Bacteria in Cancer Prevention". Microbes and Infection, 2, 2000, 681-686, XP-002239621.

Ingrid Wollowski et al., "Protective Role of Probiotics and Prebiotics in Colon Cancer", Am J Clin Nutr 2001; 73(suppl): 451S-5S, XP-002239622.
Kaila Kailasapathy et al., "Survival and Therapeutic Potential of Probiotic Organisms With Reference to *Lactobacillus Acidophilus* and *Bifidobacterium* spp.", Immunology and Cell Biology (2000) 78, 80-88, XP-002239623.
A Hague et al., "The Short-Chain Fatty Acid Butyrate Induces Apoptosis in Colorectal Tumour Cell Lines", European Journal of Cancer Prevention 1995, 4, 359-364, XP009010019.
Maria Christina Marchetti et al., "Possible Mechanisms Involved in Apoptosis of Colon Tumor Cell Lines Induced by Deoxycholic Acid, Short-Chain Fatty Acids, and Their Mixtures", Nutrition and Cancer, 28(1), 74-80, 1997, XP009010020.
Reed et al., Structure-Function Analysis of Bcl-2 Family Proteins, Mechanisms of Lymphocyte Activation and Immune Regulation VI (1996) p. 99-112.
Adachi et al, "Apoptosis of colorectal adenocarcinoma induced by 5-FU and/or IFN-gamma through caspase 3 and caspase 8" Int. J. Oncol. 15(6):1191-1196 (1999).
Adams et al. "The Bcl-2 protein family: arbiters of cell survival" Science 281(5381):1322-1326 (1998).
Asano et al. "Antitumor activity of *Lactobacillus casei* (LC 9018) against experimental mouse bladder tumor (MBT-2) " J Urol. 136(3):719-721 (1986).
Ashkenazi et al. "Death receptors: signaling and modulation" Science 281(5381):1305-1308 (1998).
Aso et al. "Prophylactic effect of a *Lactobacillus casei* preparation on the recurrence of superficial bladder cancer. BLP Study Group" Urol. Int. 49(3):125-129 (1992).
Baricault et al. "Use of HT-29, a cultured human colon cancer cell line, to study the effect of fermented milks on colon cancer cell growth and differentiation" Carcinogenesis 16(2):245-252 (1995).
Blatt et al. "Signaling pathways and effector mechanisms pre-programmed cell death" Bioorg. Med. Chem. 9(6):1371-1384(2001).
Boon et al. "Cancer Tumor antigens" Curr. Opin. Immunol. 9(5):681-683 (1997).
Boon et al. "Tumor antigens recognized by T cells" Immunol. Today 18(6):267-268 (1997).
Butler et al. "Down-regulation of Fas gene expression in colon cancer is not a result of allelic loss or gene rearrangement" British Journal of Cancer 77(9):1454-1459 (1998).
Chao et al. "BCL-2 family: regulators of cell death" Annu. Rev. Immunol. 16:395-419 (1998).
Cosulich et al. "Regulation of apoptosis by BH3 domains in a cell-free system" Current Biology 7(12):913-920 (1997).
Darzynkiewicz et al. "Chapter 2—Assays of Cell Viability: Discrimination of Cells Dying by Apoptosis" Methods in Cell Biology, Academic Press, New York, N.Y., vol. 41:15-38 (1994).

(Continued)

*Primary Examiner*—Laura B Goddard
(74) *Attorney, Agent, or Firm*—Milbank, Tweed, Hadley & McCloy LLP

(57) ABSTRACT

The invention concerns the isolation of novel properties of lactic acid bacteria stains. Said novel properties are advantageously useful for preventing and treating cancer. More particularly, the invention concerns the use of lactic acid bacteria to facilitate induction of cell apoptosis of a cancer. The invention also concerns the use of lactic acid bacterial strains, such as *Lactobacillus acidophilus* and *Lactobacillus casei* in methods and compositions for preventing and treating cancer, in particular colon cancer.

15 Claims, 33 Drawing Sheets

OTHER PUBLICATIONS

Earnshaw et al. "Mammalian caspases: structure, activation, substrates, and functions during apoptosis" Annu. Rev. Biochem. 68:383-424 (1999).

Enari et al. "A caspase-activated DNase that degrades DNA during apoptosis, and its inhibitor ICAD" Nature 391(6662):43-50 (1998).

Evan et al. "A matter of life and cell death" Science 281(5381):1317-1322 (1998).

Friesen et al. "Cytotoxic drugs and the CD95 pathway" Leukemia 13(11):1854-1858 (1999).

Fuchs et al. "Mdm2 association with p53 targets its ubiquitination" Oncogene 17(19):2543-2547 (1998).

Fujita et al. "Acceleration of apoptotic cell death after the cleavage of Bcl-XL protein by caspase-3-like proteases" Oncogene 17(10):1295-1304(1998).

Fulda et al. "Cell type specific involvement of death receptor and mitochondrial pathways in drug-induced apoptosis" Oncogene 20(9):1063-1075 (2001).

Granville et al. "Apoptosis: molecular aspects of cell death and disease" Lab. Invest. 78(8):893-913 (1998).

Gross et al. "Enforced dimerization of BAX results in its translocation, mitochondrial dysfunction and apoptosis" EMBO J. 17(14):3878-3885 (1998).

Haupt et al. "Mdm2 promotes the rapid degradation of p53" Nature 387(6630):296-299 (1997).

Hengartner et al. "The biochemistry of apoptosis" Nature 407:770-776 (2000).

Hermeking et al. "14-3-3 sigma is a p53-regulated inhibitor of G2/M progression" Mol. Cell. 1(1):3-11 (1997).

Holzapfel et al. "Overview of gut flora and probiotics" International Journal of Food Microbiology 41(2):85-101 (1998).

Honda et al. "Oncoprotein MDM2 is a ubiquitin ligase E3 for tumor suppressor p53" FEBS Lett. 420(1):25-27 (1997).

Hug "Fas-mediated apoptosis in tumor formation and defense" Biol Chem. 378(12). 1405-1412 (1997).

Hupp et al. "Regulation of the cryptic sequence-specific DNA-binding function of p53 by protein kinases" Cold Spring Harb. Symp. Quant. Biol. 59:195-206 (1994).

Igney et al. "Tumor counterattack—concept and reality" Eur. J. Immunol. 30(3):725-731 (2000).

Irmler et al. "Inhibition of death receptor signals by cellular FLIP" Nature 388(6638):190-195 (1997).

Kato et al. "Antitumor activity of *Lactobacillus casei* in mice" Gann. 72(4):517-523 (1981).

Kato et al. "Effects of oral administration of *Lactobacillus casei* on antitumor responses induced by tumor resection in mice" International Journal of Immunopharmacol. 16(1):29-36 (1994).

Khaled et al. "Withdrawal of IL-7 induces Bax translocation from cytosol to mitochondria through a rise in intracellular, pH" Proc Natl Acad Sci USA 96(25):14476-14481 (1999).

Kim et al. "Reconstitution of caspase-8 sensitizes JB6 cells to TRAIL" Biochem. Biophys. Res. Commun. 277(2):311-316 (2000).

Kluck et al. "The release of cytochrome c from mitochondria: a primary site for Bcl-2 regulation of apoptosis" Science 275(5303):1132-1136 (1997).

Korsmeyer et al. "BCL-2 gene family and the regulation of programmed cell death" Cancer Res. 59(7 Suppl):1693s-1700s (1999).

Krammer "CD95(APO-1/Fas)-mediated apoptosis: live and let die" Advances in Immunology 71:163-210 (1999).

Kroemer et al. "Mitochondrial control of apoptosis" Immunology Today 18(1):44-51 (1997).

Kubbutat et al. "Regulation of p53 stability by Mdm2" Nature 387(6630):299-303 (1997).

Li et al. "Cleavage of BID by caspase 8 mediates the mitochondrial damage in the Fas pathway of apoptosis" Cell 94(4):491-501 (1998).

Li et al. "Cytochrome c and dATP-dependent formation of Apaf-1/caspase-9 complex initiates an apoptotic protease cascade" Cell 91(4):479-489 (1997).

Li et al. "Cytochrome c release and apoptosis induced by mitochondrial targeting of nuclear orphan receptor TR3" Science 289(5482):1159-1164 (2000).

Liu et al. "Expression patterns of the c-myc gene in adrenocortical tumors and pheochromocytomas" Journal of Endocrinology 152(2):175-181 (1997).

Lorenzo et al. "Apoptosis inducing factor (AIF): a phylogenetically old, caspase-independent effector of cell death" Cell Death Differ. 6(6):516-524 (1999).

Luo et al. "Bid, a Bcl-2 interacting protein, mediates cytochrome c release from mitochondria in response to activation of cell surface death receptors" Cell 94:481-490 (1998).

Luo et al. "Comparison of the effects of immunosuppressive factors from newly established colon carcinoma cell cultures on human lymphocyte proliferation and cytokine secretion" Tumour Biol. 21(1):11-20 (2000).

Macdonald et al. "Adjuvant therapy of colon cancer" Seminars in Oncoloy 28(1):30-40 (2001).

Maki et al. "In vivo ubiquitination and proteasome-mediated degradation of p53(1)" Cancer Res. 56(11):2649-2654 (1996).

Maki et al. "Ubiquitination of p53 and p21 is differentially affected by ionizing and UV radiation" Mol. Cell Biol. 17(1):355-363 (1997).

Maltzman et al. "UV irradiation stimulates levels of p53 cellular tumor antigen in nontransformed mouse cells" Mol. Cell Biol. 4(9):1689-1694 (1984).

Marzo et al. "Bax and adenine nucleotide translocator cooperate in the mitochondrial control of apoptosis" Science 281(5385):2027-2031 (1998).

Matsuzaki et al. "Anti-tumour activity of *Lactobacillus casei* on Lewis lung carcinoma and line-10 hepatoma in syngeneic mice and guinea pigs" Cancer Immunol. Immunother. 20(1):18-22 (1985).

Midgley et al. "p53 protein stability in tumour cells is not determined by mutation but is dependent on Mdm2 binding" Oncogene 15(10):1179-1189 (1997).

Minn et al. "Bcl-x(L) forms an ion channel in synthetic lipid membranes" Nature 385(6614):353-357 (1997).

Minn et al. "Recent progress on the regulation of apoptosis by Bcl-2 family members" Adv. Immunol. 70:245-279 (1998).

Miyashita et al. "Tumor suppressor p53 is a direct transcriptional activator of the human bax gene" Cell 80(2):293-299 (1995).

Momand et al. "MDM2—master regulator of the p53 tumor suppressor protein" Gene 242(1-2):15-29 (2000).

Morotomi et al. "In vitro binding of potent mutagenic pyrolysates to intestinal bacteria" J. Natl. Cancer Inst. 77(1):195-201 (1986).

Mross et al. "Chemotherapy of colonic carcinoma in the year 2001" Praxis (Bern 1994). 90(12):497-510 (2001).

Muchmore et al. "X-ray and NMR structure of human Bcl-xL, an inhibitor of programmed cell death" Nature 381(6580):335-341 (1996).

Muzio et al. "FLICE, a novel FADD-homologous ICE/CED-3-like protease, is recruited to the CD95 Fas/APO-1) death—inducing signaling complex" Cell 85(6):817-827 (1996).

Nagane et al. "The potential of TRAIL for cancer chemotherapy" Apoptosis 6(3):191-197 (2001).

Nicoletti et al. "A rapid and simple method for measuring thymocyte apoptosis by propidium iodide staining and flow-cytometry" Journal of Immunological Methods 139:271-279 (1991).

Nita et al. "5-Fluorouracil induces apoptosis in human colon cancer cell lines with modulation of Bcl-2 family proteins" British Journal of Cancer 78(8):986-992 (1998).

Nunez et al. "Caspases: the proteases of the apoptotic pathway" Oncogene 17(25):3237-3245 (1998).

Ozoren et al. "Homozygous deletion of the death receptor DR4 gene in a nasopharyngeal cancer cell line is associated with TRAIL resistance" Int. J. Oncol. 16(5):917-925 (2000).

Park et al. "Protein kinase C activation by PMA rapidly induces apoptosis through caspase-3/CPP32 and serine protease(s) in a gastric cancer cell line" Int. J. Oncol. (2001) 18(5):1077-1083.

Perdigon et al. "Prevention of gastrointestinal infection using immunobiological methods with milk fermented with *Lactobacillus casei* and *Lactobacillus acidophilus*" J. Dairy Res. (1990) 57(2):255-264.

Peters et al. "Molecular downstream events and induction of thymidylate synthase in mutant and wild-type p53 colon cancer cell lines after treatment with 5-fluorouracil and the thymidylate synthase inhibitor raltitrexed" Eur. J. Cancer 36(7):916-924 (2000).

Price et al. "Increased sequence-specific p53-DNA binding activity after DNA damage is attenuated by phorbol esters" Oncogene 8(11):3055-3062 (1993).

Ragnhammar et al. "A systematic overview of chemotherapy effects in colorectal cancer" Acta Oncologia 40(2-3):282-308 (2001).

Reed "Double identity for proteins of the Bcl-2 family" Nature 387(6635):773-776 (1997).

Renner et al. "The possible role of probiotics as dietary antimutagen" Mutat. Res. 262(4):239-245 (1991).

Rich et al. "Defying death after DNA damage" Nature 407(6805):777-783 (2000).

Roa et al. "p53 gene mutation in cancer of the colon and rectum" Rev. Med. Chil. 128(9):996-1004 (2000).

Rosse et al. "Bcl-2 prolongs cell survival after Bax-induced release of cytochrome c" Nature 391(6666):496-499 (1998).

Ryu et al. "Increased expression of cFLIP(L) in colonic adenocarcinoma" J. Pathol. 194(1):15-19 (2001).

Sakahira et al. "Cleavage of CAD inhibitor in CAD activation and DNA degradation during apoptosis" Nature 391(6662):96-99 (1998).

Salminen et al. "Clinical uses of probiotics for stabilizing the gut mucosal barrier: successful strains and future challenges" Antonie Van Leeuwenhoek 70(2-4):347-358 (1996).

Salvesen et al. "Caspases: intracellular signaling by proteolysis" Cell 91(4):443-446 (1997).

Sarin et al. "Target cell lysis by CTL granule exocytosis is independent of ICE/Ced-3 family proteases" Immunity 6(2):209-215 (1997).

Shackelford et al. "Effect of feeding fermented milk on the incidence of chemically induced colon tumors in rats" Nutr. Cancer. 5(3-4):159-164 (1983).

Sharma et al. "Death the Fas way: regulation and pathophysiology of CD95 and its ligand" Pharmacol. Ther. 88(3):333-347 (2000).

Shieh et al. "DNA damage-induced phosphorylation of p53 alleviates inhibition by MDM2" Cell 91(3):325-334 (1997).

Shimizu et al. "Bcl-2 family proteins regulate the release of apoptogenic cytochrome c by the mitochondrial channel VDAC" Nature 399(6735):483-487 (1999).

Sionov et al. "The cellular response to p53: the decision between life and death" Oncogene 18(45):6145-6157 (1999).

Solovyan et al. "Distinct mode of apoptosis induced by genotoxic agent etoposide and serum withdrawal in neuroblastoma cells" Molecular Brain Research 62(1):43-55 (1998).

Song et al. "Soluble Fas ligand released by colon adenocarcinoma cells induces host lymphocyte apoptosis: an active mode of immune evasion in colon cancer" British Journal of Cancer 85(7):1047-1054 (2001).

Suzuki et al. "IL-6 and IFN-gamma regulation of IL-10 production by human colon carcinoma cells" Int. J. Oncol. 18(3):581-586 (2001).

Vander et al. "Bcl-xL regulates the membrane potential and volume homeostasis of mitochondria" Cell 91(5):627-637 (1997).

Vermijlen et al. "Perforin and granzyme B induce apoptosis in FasL-resistant colon carcinoma cells" Cancer Immunol. Immunother. 50(4):212-217 (2001).

Walczak et al. "The CD95 (APO-1/Fas) and the TRAIL (APO-2L) apoptosis systems" Exp. Cell Res. 256(1):58-66 (2000).

Wang et al. "Increased and altered DNA binding of human p53 by S and G2/M but not G1 cyclin-dependent kinases" Nature 376(6535):88-91 (1995).

Yamada et al. "TRAIL Causes Cleavage of Bid by Caspase-8 and Loss of Mitochondrial Membrane Potential Resulting in Apoptosis in BJAB Cells" Biochemical and Biophysical Research Communications 265(1):130-133 (1999).

Yang et al. "A novel Bcl-x isoform connected to the T cell receptor regulates apoptosis in T cells" Immunity 7(5):629-639 (1997).

Zha et al. "Serine phosphorylation of death agonist BAD in response to survival factor results in binding to 14-3-3 not BCL-X(L)" Cell 87(4):619-628 (1996).

Zoratti et al. "The mitochondrial permeability transition" Biochimica et Biophysica Acta 1241(2):139-176 (1995).

Zou et al. "Apaf-1, a human protein homologous to C. elegans CED-4, participates in cytochrome c-dependent activation of caspase-3" Cell 90(3):405-413 (1997).

\* cited by examiner

A) Control

B) 5FU (100 µg/mL)

C) Live bacteria $10^8$

D) Live bacteria $10^8$ + 5FU

5FU

5FU + live bacteria

5FU + heated bacteria

5FU

5FU + live bacteria

5FU + heated bacteria

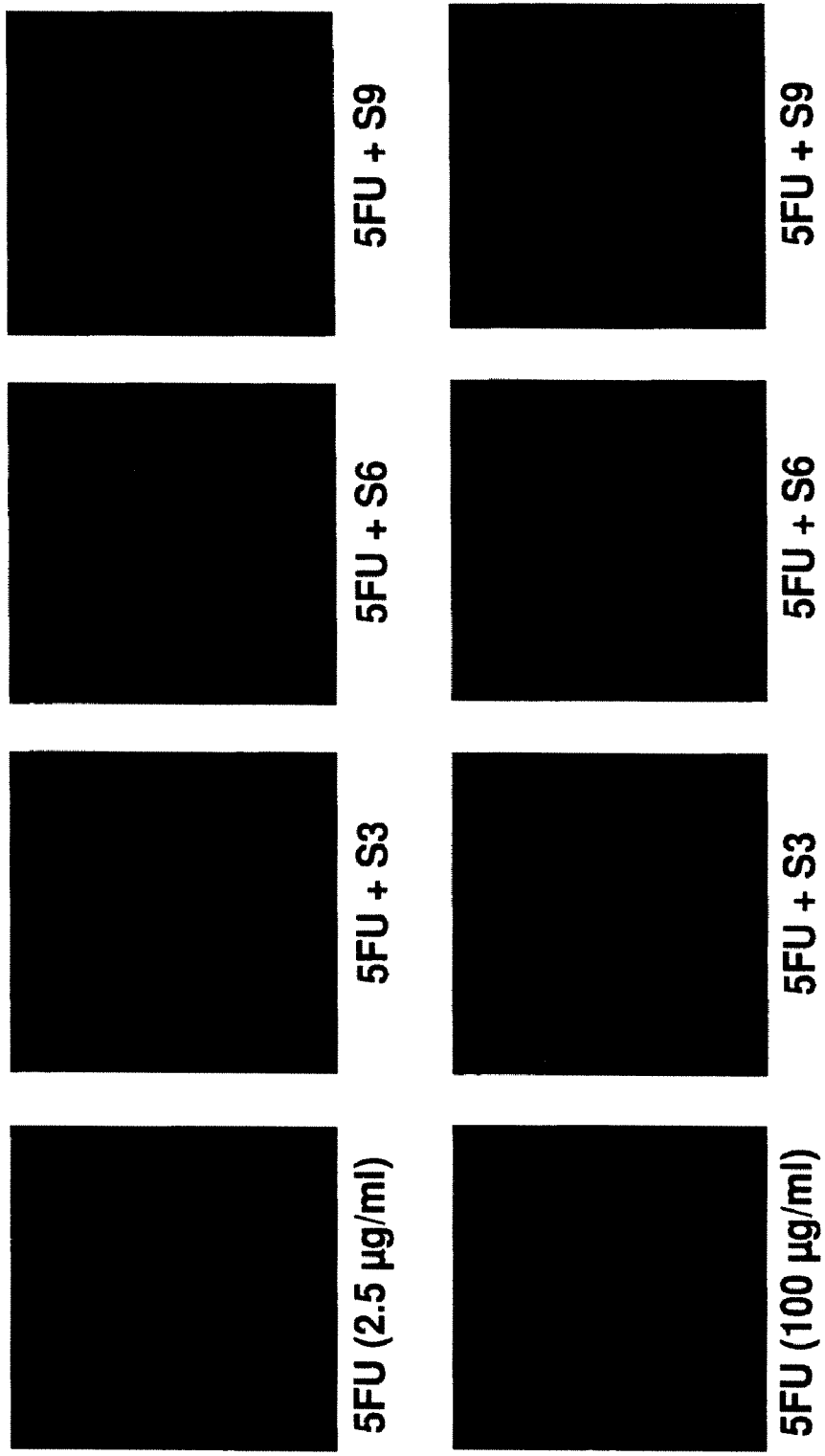
FIG. 28 (CON'T)

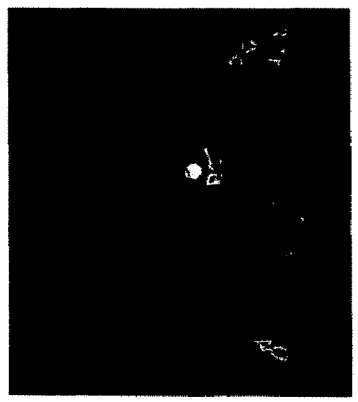
Ctrl +Serum
Ctrl -Serum
(630X)
S9
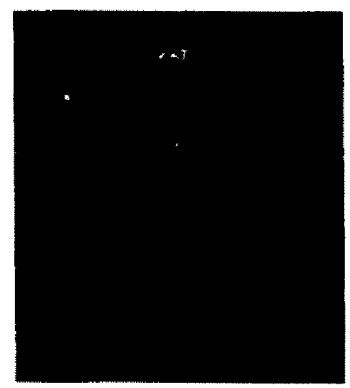
S6
S3
FIG. 28 (CON'T)

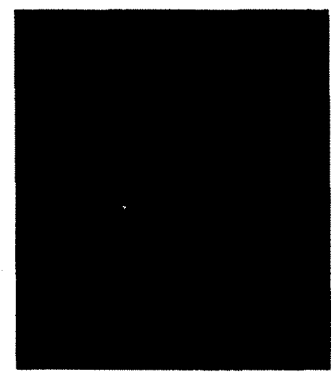
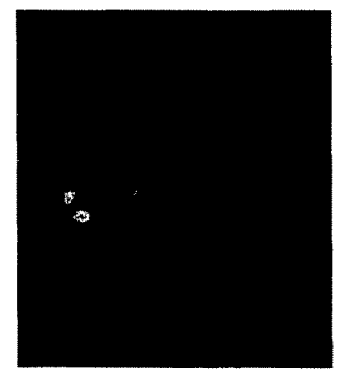
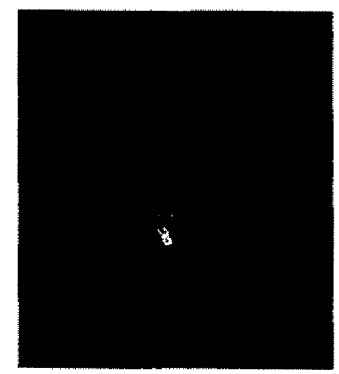
FIG. 28 (CON'T)

LACTIC ACID BACTERIA AND THEIR USE IN THE TREATMENT OF CANCER

INCORPORATION OF SEQUENCE LISTING

Two paper copies of the sequence listing (Sequence Listing No. 1 and Sequence Listing No. 2) and a computer-readable form of the sequence listing on 3.5 floppy disk containing the file named Sequence Listing.txt, as modified on Apr. 6, 2005, are herein incorporated by reference.

AREA OF INVENTION

The present invention concerns highlighting the utility of lactic bacteria strain in the prevention and treatment of cancer. More specifically, the present invention concerns the use of lactic acid bacteria to facilitate the induction of cellular apoptosis of a cancer.

DESCRIPTION OF PRIOR ART

*Lactobacillus acidophilus* I-1492 bacteria as present in the Bio-K+product and subject of patent request PCT/CA97/00915 are recognised to have a beneficial effect on blood cholesterol levels in mammals.

The international application no. WO 98/23727 has as an object a lactic ferment which comprises a strain of *Lactobacillus acidophilus* I-1492. As such, these bacteria are mainly used for the preparation of lactic ferment in order to reduce blood cholesterol levels in mammals.

In addition, these bacteria are also known to possess properties that have the effect of strengthening the immune system, facilitating nutrient absorption and stimulating the intestinal flora. It is known that lactic acid bacteria have a positive effect on the intestinal flora and also on the immune system. Indeed, lactic acid bacteria allow stimulation of the immune system which thus has the effect of providing a better defense at the level of the digestive system. These bacteria are also known to neutralize secondary effects caused by various antibiotics.

In the country, a good number of people die every year of colon cancer. Cancer is the third disease that causes the most deaths per year. In Canada, in the year 2000, the morality rate attributed to cancer was 6,500 and there are more than 17,000 new cases.

The use of neutraceuticals involving the administration of yogurt and/or of fermented milk as a complementary treatment against cancer is also known.

The treatment which is already used as therapy in humans is the ablation of the cancerous mass by surgery and then there may be irradiation of the area where the cancer was found in order to avoid leaving traces of unwanted cells.

Chemotherapy also exists. This treatment involves the administration of anticancer agents such as 5-fluoro-uracil (5FU). This compound is combined with an adjuvant to limit the negative effects of chemotherapy. 5-fluoro-uracil is a medicament that is commonly used to treat colon cancer. This medicament may be administered orally or intra peritoneally (as close as possible to the cancerous target) given its large instability in serum. It is known for causing death in cancerous colon cells by different means.

The death of a cell, also named apoptosis, may be executed with the use of different proteins. For example, cellular apoptosis can result from the activation of a membrane receptor or from the cytoplasmic expression of different proteins favoring this phenomenon. On this subject, it is known that 5FU increases the expression of p53 protein as well as the expression of the Fas membrane receptor.

1 Generalities on Apoptosis 1.1 Definition of Apoptosis

Discovered and rediscovered many times by different cytologists and biologists, programmed cell death has acquired different names throughout the last two centuries. In 1972, the term apoptosis was finally adopted and invented by Currie and his colleagues in order to describe a frequent model of programmed cell death which the authors had observed repeatedly in several tissues and cell types. It was observed that dying cells shared many morphological characteristics which are different from the characteristics observed in cells afflicted by a pathology and in necrotic cells; and the authors suggest that these shared morphological characteristics could be the result of a common and preserved cell death program.

1.2 Role of Apoptosis

Researchers have discovered that the cells of our body can kill themselves, they know that this cellular "suicide", called "apoptosis", is essential to the organism. Apoptosis is as fundamental for the physiology of cells and tissues as cellular division and differentiation are. Apoptosis is the most common form of physiological cell death which occurs at different time, for example, during embryonic development, during tissue reorganisation, during immunological regulation and during tumoral regression. Hence, physiological cell death is a spontaneous process of cellular elimination, allowing to ensure cellular renewal, and which intervenes in the maintenance of cellular and tissue homeostasis in a manner opposite to mitosis. It is the innate mechanism by which the organism eliminates unwanted cells. Each cell contains within itself the genetic mechanism of its own destruction. The cell remains alive only at the condition that it receives the survival signals emitted by its environment. If the cell perceives signals which instruct it to commit suicide, it thus engages the death program. A malfunction at the level of the equilibrium between the proteins maintaining the cell alive and the proteins leading to cell death can be associated with a large spectrum of diseases including cancer, neurodegeneration, autoimmune diseases, diabetes, and other disorders.

2 Morphological Characteristics of Apoptosis and Necrosis 2.1 Apoptosis

One of the key characteristics of apoptosis is cellular shrinking. While cellular shrinking occurs, the cytoplasm compresses itself and the nuclear chromatin condenses and forms aggregates in the nucleus, which then stick against the nuclear membrane. The cellular organelles, such as the mitochondrion, on the other hand, appear relatively unchanged. Afterwards, the nucleus becomes fragmented. The formation and the emission of buds are observed at the surface of the cell. The integrity of the plasma membrane, even if the permeability increases, is nonetheless preserved all along the process. During the final stage of apoptosis, the cell breaks up into many vesicles containing a variety of intact organelles and nuclear fragments. The apoptotic cellular fragments are rapidly engulfed by surrounding phagocytic cells such as the macrophage. Apoptosis constitutes a so-called "clean" death since cellular fragments are rapidly eliminated. There is no inflammatory phase, nor lesion of the surrounding tissue and this in part because their cellular membrane remains intact. In summary, the morphological changes characteristic of apoptosis are cytoplasmic shrinking, DNA condensation and fragmentation and finally the formation of apoptotic body containing nuclear fragments surrounded by the cytoplasm and the cellular membrane.

2.2 Necrosis

Necrosis refers to a sudden death taking place after an extreme physical or chemical stress. It is marked by different morphological criteria. During necrosis, this uncontrolled cell death, there is a rapid loss of control of the ionic flux leading to the penetration of water and an increase in ionic influx, the cells expand as well as its organelles like the mitochondrion and the endoplasmic reticulum until the bursting of the membranes and the non-specific fragmentation of DNA into the nucleus. The release of the cytoplasmic contents to the outside in addition to other events, most often provokes lesions in the tissues located in proximity and induces a very pronounced local inflammatory response.

TABLE 1

Main differences between necrosis and apoptosis

| Characteristics | Necrosis | Apoptosis |
| --- | --- | --- |
| Tissue distribution | Cellular grouping | Isolated cells |
| Tissue reaction | Lysis and cellular content release leading to surrounding tissue inflammation | Phagocytosis of apoptotic bodies by macrophages or by surrounding cells and absence of inflammation |
| Cell Morphology | Expansion | Shrinking, loss of contact with surrounding cells, "blebbing", apoptotic body formation |
| Organelles | Damaged | Intact |
| Nucleus | Disintegrated | Condensed and fragmented |
| Lysosomes | Damaged | Intact |
| Mitochondria | Defective, ATP deficient, swollen and damaged | Swollen, change, may break, cytochrome c release |
| Biochemistry DNA | Non specific degradation | Intranuclear cleavage |
| Proteins | Non specific degradation | Caspase activation |

3 Different Stages of the Apoptotic Process

Apoptosis can have three different stages (FIG. 2). First the cell must receive an apoptotic signal therefore the activation or the commitment phase. Then, there is a regulation or a control phase; and finally an execution phase during which the intracellular enzymatic cascade inducing apoptotic cell death takes place.

3.1 Apoptosis Activation Stage

A variety of stimuli, internal as well as external, can activate the cell to become apoptotic. Among the different stimuli, one can enumerate biological agents (membrane receptors, transcription factors, oncoproteins, viral infections, bacterial toxins, . . . ), suppression of factors that are essential to cellular growth (cytokines, growth and nutritive factors, . . . ), genomic DNA lesions (spontaneous or provoked), exposure to chemical substances (cancer causing agents) exposure to physical inductors (UV rays, X-rays, microwaves, heat, . . . ). This phase continues through many biochemical modifications.

3.2 Apoptotic Decision or Execution Stage

Following these different stimuli, the cell receives the different signals and decides to become apoptotic or not. This stage involves various signal transduction pathways amongst others the activation (or inactivation) of serine/threonine and tyrosine kinases and phosphatases, secondary messenger synthesis, gene modification and expression, and the activation of specialized proteases known by the name of caspases. The final decision to become apoptotic depends on many factors including the equilibrium between the pro- and anti-apoptotic proteins (the family of Bcl-2 proteins), the metabolic state of the cell and also the stage of the cell cycle in which the cell is. Many arguments suggest that the progression of this second stage is controlled by the family of Bcl-2 proteins, which are generally associated to the external membrane of the mitochondria, of the endoplasmic reticulum, and of the nucleus. The family of Bcl-2 proteins is divided into two groups of proteins, the first inhibit apoptosis (Bcl-2, Bcl-$X_L$, Bcl-w, CED-9, . . . ) and the others favor apoptosis (Bax, Bid, Bad, Bak, Bcl-$X_S$, . . . ). Being pro- or anti-apoptotic, they have the ability to control the ionic flux between various cellular compartments, especially between the mitochondria and the cytoplasm. At this same stage, there is activation of the caspases in the form of an amplification system by auto-activation by the cells themselves and between each other and also by the release of apoptotic activation factors like AIF (apoptosis-inducing factor) and cytochrome c from the mitochondria. The intermembrane space of the mitochondrion comprises many proteins which participate in the activation of apoptosis, like pro-caspase-2, -3, -7 and -9, AIF and cytochrome c. The activation of these caspases will lead to a point of no return since, by their activation, they will cleave their different targets, amongst others, the proteins necessary for cell survival.

3.3 Apoptotic Degradation Stage

The cell is now irreversibly engaged in the cell death program that consists in the presentation of morphological characteristics of the apoptotic signature. Therefore, by the activation of the different caspases, many proteins necessary for cell survival are cleaved and become non-functional, like the poly(DNA-ribose) polymerase. Other caspase targets may be activated by them, amongst others, DNases which will cut up the chromatin into high molecular weight fragments.

4 Proteins Involved in the Mechanisms of the Regulation of Apoptosis

4.1.1 Family of Bcl-2 Proteins

The Bcl-2 protein and this protein of the same family are important apoptosis modulators. In this protein family, there are two classes including the anti-apoptotic proteins (Bcl-2, Bcl-$X_L$, Mcl-1, Bcl-w, Bfl-1/A1, Brag-1) and the pro-apoptotic proteins (Bax, Bak, Bad, Bid, Bik, Bim, Bcl-$X_S$) (Reed, 1996). The members of the Bcl-2 family are classified by the number of domains homology with Bcl-2 (BH:Bcl-2 homology). The Bcl-2 protein contains 4 domains. All the anti-apoptotic proteins have the four domains, whereas the pro-apoptotic proteins can be divided in three categories. One group contains the BH1, BH2 and BH3 domains (Bax, Bad), whereas the other group contains only the BH3 domain (Bad, Bid, Bik). Bcl-Xs form$_s$ its own group, containing the BH3 and BH4 domains. A crystallography study allowed to determine the structure of the Bcl-$X_L$ protein. The protein is therefore formed by two central α-helices surrounded by five amphipathic α-helices. It is interesting to note that the tridimensional structure is homologous to bacterial toxins forming pores in membranes, like the diphtheria toxin and colicin, which may suggest a potential action mechanism of these proteins at the mitochondrial level. Another structural characteristic is the capacity of these proteins to homo- and heterodimerize with one another through their BH3 domain, as such, they may favor or antagonize their functions between each other.

4.1.2 Roles of the Pro- and Anti-Apoptotic

A—On the mitochondrion

First of all, a description of the modifications that the mitochondrion goes through during apoptosis. The isolated mitochondria in a situation of apoptosis goes through what is known as a mitochondrial permeable transition (MPT). Experimentally, MPT is characterized by an abrupt increase in the internal membrane permeability to particles with a molecular weight of $\leq 1500$ Da. This transition in permeability has many consequences including the collapse of $\Delta\psi_m$, osmotic swelling, release of matrix $Ca^{2+}$, the creation of oxygen-reactive species, and the rupture of the external membrane of the mitochondrion leading to the release of cytochrome c from the inter-membrane space of the mitochondrion. A biochemical characterization of the mitochondrion has allowed to identify $Ca^{+2}$ and voltage-sensitive pores which control MPT, which will be named PT pores. The pores are localized at the junction of the internal and external membranes of the mitochondrion, and as such, the opening of the pores allow direct communication between the matrix of the mitochondrion and its environment. The "voltage-dependent anion channel" (VDAC) and the "adenine nucleotide translocator" (ANT) are part of the PT pores.

The proteins of the Bcl-2 family have various cytoplasmic distributions. The Bcl-2 and Bcl-x proteins, have a hydrophobic C-terminal tail containing a membrane insertion sequence, and the majority of these proteins are recognized to be associated to the membranes of the mitochondria, of the endoplasmic reticulum, and to the nuclear membrane. In their inactive form, the pro-apoptotic proteins, Bad, Bax and Bid, have a location which is primarily cytoplasmic. However, during their activation, they are relocated on the mitochondria. When Bid is cleaved, its COOH terminal is relocated to the surface of the mitochondrion. The action of these proteins, either to prevent or to initiate apoptosis, is located at the level of the mitochondria, however the mechanism of these actions remains controversial and uncertain. It has been demonstrated that by adding the protein Bax, a pro-apoptotic protein, to isolated mitochondria, there is induction of cytochrome c release, whereas over expression of Bcl-2 or Bcl-X protein prevents the release of cytochrome c thus blocks apoptosis. It is clear that the Bcl-2 family is implicated very narrowly in the liberation of cytochrome c, the electron transport protein within the mitochondrion. In addition to its implication in oxidative phosphorylation in the mitochondrion, cytochrome c (as well as the adaptor protein Apaf-1) is one of the components required for caspase-9 activation in the cytosol. How can the members of the Bcl-2 family regulate the release of cytochrome c? Many hypotheses have been put forth, however none has been definitively proven. There are three basic models that may be suggested.

1—The members of the Bcl-2 family form a channel which facilitates the transport of proteins. Based on the structural similarity between the Bcl-$X_L$ and the sub-unit of the diphtheria toxin which form pores, it has been suggested that the Bcl-2 proteins may insert themselves in the external membrane of the mitochondrion, where they may form a channel or even a big hole. The members of the Bcl-2 family may indeed insert themselves in synthetic bi-lipid layer, oligomerize, and form a channel with a discrete conduction. The Bid and Bik proteins may directly induce the mitochondrion to release cytochrome c without interacting with VDAC or ANT suggesting that they act outside of the PT pores.

2—The members of the Bcl-2 family interact with other proteins to form channels. The family of Bcl-2 proteins interacts with many proteins. One possibility is that the members of the family of pro-apoptotic protein recruit other proteins from the external mitochondrial membrane in order to form a pore large enough to form a channel. A particularly interesting candidate for such a protein would be the voltage dependent anion channel (VDAC), many members of the Bcl-2 family can bind to it and regulate its channel activity. Since the characterized size of the pore of the VDAC channel is too small to let the proteins through, this model must assume that the VDAC goes through a conformational change after binding of members of the Bcl-2 family. It has been demonstrated that the Bcl-2 and Bcl-XL proteins favor the closing of the PT pores, whereas the pro-apoptotic protein Bax has the contrary effect; it interacts with ANT and VDAC to favor the opening of these pores and the anchoring of cytochrome c.

3—The Bcl-2 family members induce a rupture in the external membrane of the mitochondrion. It is possible that the Bcl-2 family controls the homeostasis of the mitochondrion. In this model, the apoptotic signal would alter the physiology of the mitochondrion (for example ionic exchange or oxidative phosphorylation) such as the organelle swellings, which results in the physical rupture of the external membrane and the re-dumping of proteins located between the membranes of the mitochondria, in the cytosol. The need to form a channel big enough to let cytochrome c go through is now not necessary since the proteins would simply diffuse through the tears in the double lipid layer.

The pro-apoptotic proteins (Bid) may homodimerize to form a pore to let the cytochrome c exit. The anti-apoptotic proteins (Bcl-2) have the capacity to bind with PT pores and thus prevent the re-dumping of inter-membrane proteins, however, the pro-apoptotic proteins (Bax), will allow the opening of PT pores.

The AIF (for apoptosis-inducing factor) protein which has been identified and its gene cloned, is capable, by itself, to induce apoptosis in the isolated nuclei. This molecule is synthesized in the cytosol under a precursor form and is then imported into the mitochondrion. Like cytochrome c, this is a phylogenetically ancient molecule, with a double function; oxydoreduction and apoptogenetic factor. However, in contrary to the pathway of cytochrome c, which necessitates the activation of other factors to induce apoptosis, the pathway of AIF is instead independent of caspases and does not necessitate any intermediate in order to provoke apoptosis. This constitutes amongst others a prototype of the apoptotic pathways independent of caspases.

The hypothesis concerning inhibitory apoptotic mechanisms and in particular the sequestration of Apaf-1 by Bcl-2 and its anti-apoptotic agonists seems to still be discussed. Apaf-1 is probably an important target of the Bcl-2 family members, since Apaf-1 deficient cells are refractory to different pro-apoptotic signals that are themselves inhibited by Bcl-2. In addition, an over expression of Apaf-1 has demonstrated that this protein was associated with survival proteins like Bcl-$X_L$ and Bcl-2. Also it has been shown that no co-immunoprecipitation between the members of the Bcl-2 family and Apaf-1 exists. Apaf-1 has also been found at the level of sites where the survival proteins like Bcl-2 and Bcl-$X_L$ reside, like external mitochondrial membranes, the nuclear membrane and the endoplasmic reticulum.

4.1.3 Modulation Mechanisms of the Proteins of the Bcl-2 Family

Many different mechanisms exist to modulate the functions of pro- and anti-apoptotic proteins. Firstly, the state of dimerization of members of the Bcl-2 family affects their activity. One of the functions of anti-apoptotic proteins Bcl-2 and Bcl-$X_L$ is to dimerize with the pro-apoptotic protein Bax in order to neutralize its activity. By being a heterodimer, Bax is inactive, but once it is free to dimerize with itself, Bax is able to induce apoptosis. Bid, Bik and Bad may act by inhibiting the apoptotic action of Bcl-2 and Bcl-$X_L$ by forming heterodimers. Secondly, altering the expression level of pro- and anti-apoptotic members of the Bcl-2 family may either initiate or inhibit apoptosis. For example, when the number of Bcl-2 is larger than or equal to the number of Bax, the cell in question is protected from apoptosis. However, when the number of Bax exceeds the number of Bcl-2, the cell is more subject of becoming apoptotic. Thirdly, the proteins of the Bcl-2 family may be modified by phosphorylation. The best example for this would be the pro-apoptotic protein Bad. In its non-phosphorylated state, it dimerizes with Bcl-2 and Bcl-$X_L$ thereby neutralizing its anti-apoptotic activity. On the other hand, when Bad is phosphorylated, it is sequestered and hence cannot interact and neutralize Bcl-2 and Bcl-$X_L$. Fourthly, the Bcl-2 family can be modified by cleavage. When apoptosis is caused by Fas, it has been demonstrated that the caspases would cleave Bcl-2 and Bcl-$X_L$ and the cleaved products are no longer protectors and even become pro-apoptotic. Bid is another protein of the Bcl-2 family which is activated by the cleavage of the caspases. While the protein in its entire length is inactive, following cleavage caused the by caspase 8, Bid induces the re-dumping of cytochrome c by the mitochondrion. Finally, the conformation of Bcl-2 proteins modifies their activity. The best evidence for this mechanism comes from the studies done on Bax. In its inactive state, Bax exists in a conformation in which it resists proteolytic cleavages. However, following its activation and its re-localization on the mitochondrion, the N-terminal region of the protein becomes susceptible to cleavages, suggesting that a conformational change indeed occurs.

To summarize, the mitochondria have an important place in the launching of apoptosis. Their inter-membrane space contains many proteins (cytochrome c, caspase-2, -3, -7, and -9, AIF) which once released in the cytoplasm participate in the degradation phase of apoptosis. The enigma of the induction mechanisms and of the apoptosis control mechanisms by the mitochondria rests on four essential points: the molecules of the Bcl-2/Bcl-$X_L$ family which could contribute to the formation of ion channels at the level of intracellular membranes. The pro-apoptotic members of this family (like Bax, Bid, . . . ) may also intervene in the permeability of the PT pores of the mitochondrial membrane, notably as apoptosis activator proteins. Lastly, the anti-apoptotic molecules of the Bcl-2 family may also act by titrating endogenous activators (like Apaf-1) of apoptosis. A last point is that certain pro-caspases also have a mitochondrial localization. As such, the apoptotic promotors or inhibitors of the Bcl-2 family regulate apoptosis thanks to the multiple effects on the cascades of the caspases activation, on the redox potential, and on the function of the permeability barrier of the mitochondrial membranes. Overall, these observations thus suggest an implication of the transition of the permeability in the regulation of apoptosis induced by the mitochondria.

4.2 Role of Caspases in Apoptosis 4.2.1 Definition and Classification of Caspases The caspases are specialized proteases which are essential for apoptosis. They are different from other proteases because they use a cysteine for catalysis and they only cleave after aspartic acid residues. This unusual specificity of having an aspartate as a substrate is found only with another protease, the granzyme B, however this enzyme uses a serine as an active site. The caspases are synthesized as a simple chain of polypeptides and they are inactive zymogens. These zymogens are composed of three domains: an N-terminal pro-domain, and two other domains, p10 and p20, which are found in the mature enzyme. When they are activated, each polypeptide chain is cleaved into two sub-units, a large one (p20) and a small one (p10), which later dimerize. Therefore, the mature enzymes which have been observed are heterotetramers composed of two p20/p10 heterodimers and two active sites. The N-terminal peptide is cleaved and released during activation. This N-terminal peptide is not required for enzymatic activity, its role is known on caspase 8 and 10 where it acts as an interaction domain with other proteins to modulate their activation. Caspases 8 and 10 contain a "death-effector domain" (DED) whereas caspases 2 and 9 contain a caspase activation and recruitment domain (CARD).

There are at least 14 different caspases identified in mammalian tissues to this day. It is possible to divide the caspases into three different groups by their substrate specificity, that is, by their recognition of the three amino acids which precede the aspartic acid. The first group contains the caspases involved in the inflammatory process, thus activation of pro-cytokines which include caspases 1, 4 and 5. These enzymes are sometimes known as ICE-like caspases because another name for caspase-1 is "interleukin-1 converting enzyme" (ICE). The tetrapeptide motif that they recognize and prefer is WEHD, on the other hand, the ICE-like caspases are the most tolerant for what concerns amino-acid substitution when compared to signalling and effector caspases. The second group of caspases comprises the caspases 6, 8, 9 and 10. These enzymes are considered as signalling caspases because they may activate other caspases and thus begin the cascade. Their recognition motif is (LV)EXD. The last group contains the caspases 2, 3 and 7. These enzymes are known as "effector" because they cleave many cellular targets which result in the morphological appearance of apoptosis. The activation of these caspases generally end in a "point of no return" in cellular death. The effector enzymes are the most specific, with the necessity of having an aspartic acid in the first and fourth positions preceding the cleavage site. Their recognition motif is DEXD. The most recent caspases, the caspases 12-14, have not yet been characterized enough to be classified in one of the three groups.

4.2.2 Activation of Caspases

There are three different mechanisms to activate the caspases. The first mechanism is the activation of a caspase by another caspase which was activated beforehand. Most of the caspases are activated following a proteolytic cleavage of the zymogen between the p20 and p10 domains, and usually another cleavage between the pro-domain and the p20 domain. It is interesting to note that all of these cleavage sites occur after an aspartate, the substrate of caspases, which suggests the possibility of an activation by auto-catalysis. Indeed, the easiest way to activate a caspase is to put it in the presence of another caspase which is already activated. This strategy of caspase cascade is largely used by the cell for the activation of three important caspases, caspase-3, -6 and -7. These three effector caspases are considered the hardest working of the family of caspases, and are usually more numerous and active than the others.

As illustrated in FIG. 4, the first cleavage occurs between the p20 and p10 domains (here 12 kDa) in order to separate the two sub-units. The second proteolytic cleavage occurs between the pro-domain and the large sub-unit and then there is formation of a heterotetramer which leads to the mature caspase in its active form.

The caspase cascade is a very useful method to amplify the pro-apoptotic signal, but it cannot explain how the first, the most downstream of the caspases, is activated. There are at least two other models which may explain the activation of the very first caspases. The first is the induction of activation by bringing them closer. It is known that caspase-8 is the initiator caspase when apoptosis is induced by the death receptors. When the ligand binds to its receptor, the death receptor CD95/Fas trimerize and form signalling complexes bound to the membrane. These complexes recruit, by adaptor proteins, many pro-caspase-8 molecules which results in a large local concentration of zymogens. This caspase activation model through bringing them closer stipulates than under this crowded condition, the weak proteolytic intrinsic activity of pro-caspase-8 is sufficient to allow mutual cleavage of pro-enzymes and to activate one another. The last caspase activation model is the association of the pro-caspase with a regulating sub-unit. Take for example caspase-9 which necessitates an association with cofactors for its activation. The "apoptotic protease activating factor-1 (Apaf-1) cofactor" was identified by a biochemical approach as being one of the two proteins necessary for the activation of caspase-9, the other being cytochrome c. The complex formed by these three proteins, needing ATP, gives the active form of caspase-9 often called apoptosome. Therefore, Apaf-1 is not only an activating protein of caspase-9 but is a sub-unit essential to its functioning. In summary, the effector caspases are generally activated by downstream caspases, whereas the initiator caspases are activated by regulated protein-protein interactions.

4.2.3 The Victims of Caspases

The caspases cleave a good number of cellular proteins, and the process of proteolysis is limited since there are a small number of cuts that are achieved. Sometimes, the cleavages lead to the activation of the protein, and at other times, the inactivation but never the degradation since the specificity of their substrates distinguishes the caspases as being the most strict endopeptidases. The caspases cleave many cellular proteins whose number does not cease to increase. Structural, nuclear and signalling proteins are the targets of the caspases (Table 1). There are different cytoskeletal proteins cleaved by caspases, like, for example, laminin, α-fodrin, and actin. The cleavage of these proteins is probably responsible for the morphological changes observed during apoptosis, for example, the cleavage of nuclear laminins is necessary for nuclear shrinking and budding. DNA fragmentation is due to the activation of the "caspase-activated DNase" (CAD) by the caspase-3. This DNase exists in an inactive complex form with an inhibitory sub-unit, ICAD. CAD activation occurs therefore by the cleavage of the inhibitory sub-unit by caspase-3 resulting form the release and the activation of the catalytic sub-unit.

TABLE 2

A few examples of the victims of caspases

| Category | Target | Effect |
| --- | --- | --- |
| Signalling | Other caspases | Activation |
| | PKC δ | Activation, nuclear fragmentation |
| | Phospholipase A$_2$ | Activation |
| | Bcl-2, Bcl-X$_L$ | Pro-apoptotic fragment formation |
| | Bid | Activation |
| | ICAD | CAD endonuclease activation |

TABLE 2-continued

A few examples of the victims of caspases

| Category | Target | Effect |
| --- | --- | --- |
| Nuclear | DNA fragmentation factor | DNA fragmentation |
| | Of Polymerase poly (ADP-ribose) | Inactivation |
| | DNA-dependent protein kinase | Inactivation |
| | U1 (70 kDa)-snRNP | Reduction of RNA synthesis |
| | Laminin A and B | Nuclear laminin disassembly |
| Structural | Actin | Cytoskeletal rearrangement |
| | Gelsolin | Cytoskeletal rearrangement |
| | α-fodrin | Membrane change |

4.3 The p53 Protein

The p53 protein is a transcription factor which plays a critical role in cancer prevention. The p53 protein is considered as being the "guardian of the genome". This protein is a good example of how the decision between apoptosis or life can be made at an activated verification point when DNA is damaged. Depending on the stimulus and on the phase in which the cell is, the activation of p53 can lead to a halt of cellular proliferation and to the repair of DNA or to apoptosis. Whereas the first stimulus for activating p53 is damaged DNA, other cellular stresses like metabolite privation, physical damage, heat, and oxygen deprivation may also activate p53.

The level of p53 increases drastically in the few minutes following the damage that the cell has undergone. This increase is possible by post-translational modifications of the p53 polypeptide, without a clear dramatic induction of p53 mRNA following the damage caused to the DNA. The modification that occurs on the p53 polypeptide after damage to the DNA is translated by phosphorylation. In a cell not having undergone stress, the p53 protein has an extremely short half-life but becomes much more stable following a damage caused to the cell. The instability of the p53 protein in normal conditions for the cell is related to the fact that p53 is the target of proteolysis induced by small peptides, ubiquitins. Therefore, p53 is found to be tagged by the ubiquitins with the help of a protein named Mdm2, a protein that plays a role in the negative regulation of p53. It is shown that the Mdm2 protein interacts with p53 in order to become the prefect protease target by the ubiquitin. The Mdm2 protein also causes the translocation of p53 from the nucleus to the cytoplasm, where it will undergo ubiquitin-induced proteolysis. Therefore, by phosphorylation of the regulatory domain in the C-terminal portion of p53, it is shown that the activation of its binding to DNA according to specific sequences occurs. In addition, phosphorylation of serine-15 and serine-20, at the N-terminal of p53, causes the inhibition of the interaction between p53 and Mdm2 consequently increasing the level of p53 and converting it into a form which is capable of transcriptional activity. A large number of kinases phosphorylate p53, including the kinase casein, the kinases linked to extra-cellular signals, protein kinase C and the kinase Raf-1. Once phosphorylated, p53 acts like a transcription factor to increase and decrease the transcription of many genes involved in apoptosis.

Many regulating proteins of the cellular cycle are induced by p53, for example p21, GADD45 and members of the 14-3-3 family. The ability of p53 to induce stopping of the cellular cycle in the $G_1$ phase following DNA damage is well known and may be explained by the fact that the p53 protein, once stimulated, has a transcriptional activity which allows transcription of the inhibitory gene of the cyclin-dependant kinase (Cdk), the p21 protein. An elevated number of p21 will then inhibit the cyclin kinases E/Cdk2 and cyclin A/Cdk2, thus preventing these kinases of promoting the progression of the cellular cycle. In addition, the p53 protein is also involved in stopping the cellular cycle in the $G_2$ phase partly because p53 induces the expression of the protein sigma 14-3-3 which will cause the sequestration of the cyclin complex B/Cdc2. The p53 protein may lead to apoptosis by activation of the transcription of different genes yielding proteins involved in the apoptotic process. The proteins that are induced are the protein Bax, the Fas receptor and DR5 (receptor for the death ligand TRAIL), which are all involved in the apoptotic process. It also causes the reduction of Bcl-2 mRNA expression, thereby favoring the process of apoptosis. There seems to exist an apoptotic pathway induced by p53 which does not require cytochrome c release but that always requires caspase activation. Eventhough the expression of the Bax protein is increased, it is rather located in the cytosol and no translocation on the mitochondrion is detectable. Therefore, there may exist another pathway by which the p53 protein would induce apoptosis without the release of cytochrome c.

The final results following DNA damage may be the stopping of the cellular cycle, thus of growth, or apoptosis. A damage to the DNA yields an accumulation and activation of the p53 protein (FIG. 5). Once activated, p53 has a transcriptional activity which will increase the transcription of different genes (GADD45, 14-3-3, Mdm2, p21, Bax, Fas, DR5). It can also down-regulate different genes (Bcl-2). By increasing p21 which will inhibit the cyclin-dependent kinases (cdk), the cellular cycle is thus stopped in $G_1$. The cellular cycle may also be stopped in the $G_2$ phase by the increase of the proteins GADD45 and 14-3-3 by p53. The process of apoptosis is accomplished by different proteins (Bax, Fas, DR5) that are upregulated by p53. A regulatory loop of the p53 protein is possible thanks to the increase of Mdm2, a protein that binds to p53 and favors its degradation.

4.4. Death Receptors

The death receptors are receptors located on the surface of the cell and are thus named because upon binding with their ligand, they may begin the process of apoptosis. These receptors are part of the TNF receptor family, in particular the TNF-1 receptor itself, the Fas receptor (also called CD95 or Apo-1) and also the DR-3, DR-4 and DR-5 receptors. These receptors are activated by their ligand that is soluble or membrane-bound like "tumor necrosis factor-α" (TNF-α), Fas-L and "TNF-related apoptosis inducing ligand" (TRAIL). The death receptor ligands are part of the cytokine family TNF-α, and are homotrimeric molecules. Crystallographic analyses indicate that each ligand monomer binds to a receptor which indicates that the binding of a ligand involves the trimerization of these receptors. The ligand-receptor interaction induces the trimerization of the receptor which allows the physical association of adaptor proteins with the interacting protein death domains (RIP-DD), favors recruitment and activation of proximal caspases like pro-caspase-8, -10, and -2 then capable of transmitting the death signal inside the cell. Take for example TNF-R1 receptor activation. By the binding of TNF-α to the TNF-R1 receptor, the latter trimerizes giving as a result the aggregation of death domains, allowing the recruitment of TRADD which in turn recruits the adaptor molecule TRAF2, "TNF receptor-associated factor 2", which leads to the activation of the JNK and NF-κB pathways. TRADD may also recruit FADD and RIP leading to the apoptotic process and to the activation of NF-κB respectively. RIP may also recruit RAIDD, RIP-associated ICH-1/CED-3-homologous protein with a death domain, which will then recruit caspase-2 and induce apoptosis. When we take the Fas receptor as a model of activation for apoptosis, the Fas complex and FADD will recruit pro-caspase-8 which will form the complex which will induce the death signal, "the death-inducing signal complex (DISC)". Once assembled, the DISC will cause a rapid auto-activation of caspase-8 which will activate caspase-3 and will cause apoptosis of the cell. Thus, this first path of action of the Fas receptor is a rapid pathway which short-circuits the mitochondrion and which does not necessitate the supply of other molecules because it is based on the interaction of preexisting molecules.

However, it has been shown recently that the activation of caspase-8, following Fas receptor trimerization, could also provoke the cleavage of Bid, a pro-apoptotic protein of the Bcl-2 family. This cleavage brings about the penetration of a trunkated form of Bid into the mitochondrion with, as a consequence, the exit of cytochrome c and the depolarization of the mitochondrial membrane potential and apoptosis. It is also shown that when there is activation of DR-4 and DR-5 by TRAIL, caspase 8 is activated. The pathway used has not yet been well elucidated but many confirm that there is activation of caspases-3 and -9 following the activation of caspase-8 and observe that Bid is cleaved following caspase-8 activation. It is possible that by the binding of TRAIL to the DR4 or DR5 receptors there is activation of caspase-8 by recruitment helped by an adaptor molecule which activates caspase-3 and cleaves Bid at the same time so that the latter becomes active and allows the re-dumping of cytochrome c which will have the effect of activating caspase-9 which in turn will cause an amplification of the caspase cascade and will give death to the cell.

In summary, there would thus be at least two apoptosis signal transduction pathways by certain death receptors, a rapid and direct one, the other slower and putting into play the mitochondrial relay. This is why certain authors classify cells (type I or type II) according to their mode of inducing apoptosis by Fas. Like for example, the activation of Fas, in certain cells, leads almost exclusively to the caspase cascade only (type I cells). These cells usually do not demonstrate any involvement of the mitochondria, and cellular death is not inhibited by Bcl-2 or Bcl-$X_L$. In other cells, the activation of Fas engages the pathway using mitochondria for the large part, and this following activation of caspase-8. The anti-apoptotic proteins Bcl-2 or Bcl-$X_L$ may inhibit apoptosis only in type II cells by their action of preventing the release of cytochrome c into the cytosol.

Many stimuli can initiate apoptosis, however common morphological and biochemical alterations are observed and this independently of the initial stimulus. Studies suggest that the majority of apoptotic signals converge on a limited number of pathways leading to apoptosis.

FIG. 6 shows the structure of members of the death receptors and their interactions with the principal cytoplasmic effectors implicated in the apoptotic pathways. The red arrows indicated a direct activation of caspase-8, and the black arrows an inhibition of apoptosis with intermediate stages (activation of kinases/transcription factor). The abbreviations mentioned in this figure have the following meaning: DD, death domain; TRADD, TNF-receptor associated death domain; FADD, Fas-associated death domain; DISC, death-inducing signalling complex; RIP, receptor-interacting protein; TRAF2, TNF-receptor associated factor-2; NF-κB, nuclear factor kappa B, I-κB, inhibitory kappa B; JNKK, JNK kinase; TNF, tumor necrosis factor; TNFR, TNF receptor; Fas L, Fas ligand; TRAIL, tumor necrosis factor-related apoptosis inducing ligand; DR4-5, death receptor 4-5; DED, death-effector domain; RAIDD, RIP-associated ICH-1/CED-3-homologous protein with a death domain.

The process of apoptosis requires the participation of many pathways in order to activate the caspases (FIG. 7). The two most well known and best characterized pathways are apoptosis signal transduction by the death receptors and the other pathway more internal to the cell is apoptosis induced by the changes in mitochondrial integrity, particularly the release of apoptogenetic factors like cytochrome c and AIF. There exists interconnections between these two signalling pathways and signal amplification loops. Abbreviations: AIF: apoptosis-inducing factor; tBid, trunkated protein.

4.5 Protein Kinase C and Nurr77

The kinase C proteins (PKC) are part of a family of serine/threonine kinase. There are at least 11 different isoenzymes of PKC that we can divide into three sub-groups, based on their structure and their response mechanism to regulatory factors. The conventional PKC ($\alpha$, $\beta$I, $\beta$II, $\gamma$) are $Ca^{2+}$-dependent and are activated by diacylglycerol (DAG) or by 12-o-tetradecanoylphorbol-3-acetate (PMA) in an in vivo fashion. The second sub-group ($\delta$, $\epsilon$, $\eta$, $\theta$, $\mu$), the new iso-types, does not respond to $Ca^{2+}$ but is activated by DAG and PMA. The last sub-group ($\lambda$, $\xi$, $\iota$), the atypical PKC, are insensitive as much to $Ca^{2+}$ as to DAG. The PKC are responsible for the transduction of many cellular signals during a variety of cellular processes such as cellular growth, differentiation, malign transformation and apoptosis. The PKC are also known to modulate the activity of many different membrane proteins like the transport proteins, the channels, and the cytoskeleton-related membrane proteins. Since they have different roles, we notice that their activation can give different results which may even be opposite results. It has been demonstrated that PKC activation induces apoptosis in a line of gastric cancer cells treated with PMA and this through the intermediate of caspase-3 and serine proteases. It has also been demonstrated that PKC inhibits Fas receptor induced apoptosis and by the modulation of potassium ($K^+$) loss and the inhibition of caspase-8 and -3 activity. It is demonstrated by different researchers that the PKC have a role in transcriptional regulation of Fas and FasL gene expression. Park's team has demonstrated that the ability of PKC to induce Fas expression is possible thanks to the TDAG51 gene (T-cell death-associated gene) in wild type cells only. There exists another mediator in the Fas/FasL expression system that is a member of the orphan nuclear steroid receptor superfamily Nurr77. Nurr77 plays a role in cellular growth by its role as a nuclear transcription factor. It has been shown that by adding Nurr77 in its transgenic form to thymocytes, an increase of Fas ligand is obtained which suggests that Nurr77 may lead cells to become apoptotic by the induction of Fas ligand expression. Another role was identified for Nurr77. Nurr77 would be able to regulate apoptosis by a means independent of its transcriptional regulation activity, among other things by its re-localization from the nucleus towards the mitochondria causing the release of cytochrome c. Therefore, by its role as a transcription factor and its role as a protein causing the release of cytochrome c, Nurr77 can thus bring a cell to become apoptotic.

5 Colon Cancer and Defence Mechanisms

Within a tissue, homeostasis is maintained by the balance between cellular growth and programmed cell death. A cancerous cell may be defined as a cell which has survived the apoptotic process and may belong to the portion of cells that may contribute to tumor formation. Many causes can lead to cancer, as much a flaw in the growth process as a flaw in the apoptotic process. These flaws are responsible for many diseases including cancer. An accumulation of cells may occur when the death rate is normal but the growth rate is abnormally high or when the growth rate is normal but the death rate is abnormally low. Malignant cellular transformation and tumoral progression are complex processes which necessitate many genetic alterations.

Normally, tumoral cells are eliminated by presentation, at the membrane surface of antigens to cytotoxic T lymphocyte (CTL) and to "natural killer" (NK) of major histocompatibility complex class I (MHC I) at their surface thereby allowing the activation of the immune response. The cytotoxic cells can recognize tumoral cells by the expression, on their surface, of viral antigens (non-self, neo-antigens (issued from mutated self-proteins), non-mutated but over-expressed self antigens, oncofeotal antigens (gene silenced during embryogenesis which would be spontaneously re-transcribed).

Sometimes, the tumoral cells develop alternatives in order to evade the immune response. Various mechanisms are created by the tumoral cell, some of which cause an aberration in cancer cells surface antigen presentation. The reduction of MHC I expression (the tumoral cell is no longer recognized by the CTL, but may be destroyed by the NK cells) and the alteration of the structure of MHC I a bad interaction between the cytotoxic cells and the tumor cells: the reduction of the secretion of co-stimulatory or adhesion molecules (which are essential in antigenic presentation, and may cause anergy), the reduction or mutation of the membrane Fas receptor and of receptors DR4 or DR5 (tumor cell less sensitive to the attack of CTL or NK). The tumor cells may also secrete cytokines which enhance their growth. A study demonstrates that in certain types of colon cancer, the production of IL-10 (which has an inhibitory effect on the production of CD4+ T cells of type Th1 and on macrophage functions) is regulated by the local production of pro-inflammatory cytokines such as IL-6 and IFN-$\gamma$. A second study on 9 colon cancer lines demonstrates that these tumor cells produce immunosuppressant factors inhibiting the proliferation of T cells.

The concept of cellular immunity is based on the capacity of cytotoxic T lymphocytes to eliminate tumor cells. CTLs act by inducing apoptosis in cancerous cells by way of two mechanisms: by the death receptors and by the perforin/granzyme B path. However, in certain cases, the tumor cells develop means to counter-attack the surveillance of the immune system and ensure that the apoptotic process is not initiated. Teams of researchers have demonstrated that cancerous colon cells can defend themselves against CTLs by surface membrane expression of Fas ligand. This causes the death of CTLs by the binding of Fas receptor on the CTL and Fas ligand of cancerous cells. On the other hand, contradictory results have refuted this hypothesis. Therefore, we can see that this hypothesis remains a controversial research topic. Another mechanism may be developed by cancerous cells in order to avoid apoptosis and neutralize CTLs: secretion of Fas ligand in soluble form. Therefore, in this scenario, the cancer cell secretes soluble Fas ligand while causing a mutation in the trans-membrane domain of the protein, thereby removing its anchoring point to the cellular membrane. Thus, the Fas ligand binds to its ligand situated on the surface of the CTL and induces apoptosis of the CTL. It has been demonstrated that in certain cases, CTLs may induce apoptosis in cancerous cells which express Fas ligand by the perforin/granzyme B mechanism. On the other hand, in other cases, the tumor cells have developed a mechanism to counter-act the perforin/granzyme B pathway's efficacy by the over-expression of the serine-protease inhibitor PI-9.

The tumoral cells may develop many mechanisms to avoid death but sometimes these mechanisms can cause the cell to commit suicide or to cause fratricidal death (the death of a neighboring cancer cell). For example, if the cell secretes Fas ligand at its surface or in a soluble form, it may bind to Fas receptors of neighboring cell or even to a Fas receptor located on the surface of the same cell.

There exists other ways for a cancerous cell to escape apoptosis, among other by the mutation of certain proteins involved in the apoptotic process like for instance the p53 protein. This protein is one of the most common targets of colon cancer. Thus, by mutation which deprives it from its functions as a guardian of the genome and of activating the apoptotic pathway; even if the cell is damaged at the DNA level by different treatments (radiotherapy and/or chemotherapy) it may still escape apoptosis. There is also the over-expression of the protein c-FLIP, which inhibits the binding between recruiting FADD proteins and between caspase-8 and FADD. It has been demonstrated that the over-expression of this protein is frequent in different types of colon cancer which may contribute to tumor transformation in vivo.

Naturally, the list of evasion mechanisms may be long because cancer cells seem to develop strategies permitting them to overcome many obstacles which we do not cease to discover.

5.1 Therapies Against Colon Cancer

The treatments against colon cancer have a high success rate when it is localized in the colon and it has not gone through the walls of the colon. We attribute this high success rate to diagnosis early in the development of the disease. According to Statistics Canada, colon cancer is the third cancer causing the most deaths in Canada per year, 6,500 deaths in the year 2000 and 17,000 new cases. Many treatments are now available in order to counter this disease.

5.1.1 Duke's Stages of Colon Cancer

The treatments are given according to the stage of the disease. There are two systems to classify at which stage a patient's colon cancer is: the Duke classification and the TNM (tumor characteristics, nodal involvement and amount of metastasis) system. The Duke classification is the most used and here is a summary: the A stage represents the phase where the colon cancer is limited to the mucous or sub-mucous membrane of the colon. Treatment options at this stage are either a colectomy when a superficial lesion is caused by the cancer, or an excision of the affected portion when a more profound lesion is caused. The post-surgical rate of survival is 90%. The B stage is measured according to the degree of invasiveness of the cancer within the organs or the tissues surrounding the tumor. The treatment for these cases is usually the excision of the tumor and considering using chemotherapy and/or radiotherapy. The survival rate figures between 70-80%. The C stage involves the invasion of lymphatic nodules and the formation of metastases in the major blood vessels. The treatments include excision of the diseased portions, chemotherapy with the combination of an adjuvant. The last stage, the D stage, distal metastases are present. Treatments include ablation of different isolated metastases (liver, lung, ovaries), as well as chemotherapy and/or palliative chemotherapy. The survival rate following this type of operation is usually less than 5 years.

5.1.2 Chemotherapy

The most common drug used for chemotherapy is of 5-fluoro-uracil (5FU) it is administrated in intravenous form. Studies have demonstrated that the use of 5FU, after the excision of the tumor, is more beneficial for patients in Duke's stage C than excision alone. With the desire to obtain the best results to vanquish colon cancer, combined treatments are prescribed to different patients in stages B or C. Many studies show that with the combination of 5FU with an adjuvant, namely levamisole or leucovorin, better results are obtained for Duke's stage C. Levamisole is known to enhance the efficacy of 5FU; with this combination, it is shown that there is a reduction in the recurrence of the cancer, and that the mechanism is probably related to macrophage activation which destroys remaining tumor cells since it seems to positively regulate the immune system. Leucovorin is a folic acid which is administered to avoid the negative hematological effects and therefore to help keep the healthy cells alive and to leave the cancerous cells susceptible to the cytotoxic action of 5FU. In general, studies agree that the treatments using a combination with an adjuvant has a positive effect on the survival rate and on the recurrence time of the tumor after the ablation of the cancer when compared to the use of 5FU alone. 5FU acts by binding to an enzyme within the cell allowing thymine synthesis during DNA replication, and inhibiting it. Consequently, the cell, unable to divide, will die. Other drugs may act against colon cancer and are currently under clinical studies, or will be shortly. The different drugs are the following: Irinotecan (Campotasar, CPT-11), Oxaliplatine, Ralitrexed and Xeloda (Capecitabine). Irinotecan acts by inhibiting topoisomerase I which is necessary to give a certain shape to the DNA during transcription, translation and replication. Oxaliplatine acts on DNA by forming bridges in the DNA and thus inhibiting its synthesis and its replication. Ralitrexed has a role similar to 5FU since it interferes in DNA synthesis by blocking the enzyme involved in thymine synthesis. Xeloda is an oral pill which is transformed into 5FU after ingestion.

5.1.3 Mechanism of Cancer Cell Destruction by Chemotherapy

When the effect on the cells of a drug is known, it is possible to understand the mechanism leading the cell to become apoptotic. Being an inhibitor of thymine synthesis, 5FU causes DNA damage during cellular division by depriving one of the four pyrimidine bases constituting DNA. By this DNA damage, 5FU is responsible of activating p53, the protein guardian of the genome. It is demonstrated that this protein, by its transcriptional activity, can modulate the expression of the different proteins involved in the process of apoptosis, for example Bax, Bak and Bcl-2. Therefore, when the expression of Bax is increased and that the expression of Bcl-2 is decreased, the chances that the mitochondrial membrane potential is lost is increased, which sets in motion the mitochondrial apoptotic process. These proteins are regulated by the p53 protein, determines the sensitivity of the cell to chemotherapy because in the majority of colon cancers, p53 is mutated. Despite the fact that p53 is mutated, it is possible to observe the death of these cells following the addition of 5FU.

It has also been demonstrated that the treatment of cancerous cells with 5FU induces Fas receptor expression and Fas ligand expression at the surface of the cancerous cells. The induction of the expression of Fas receptor thus allows a better chance of elimination of the cancerous cell by the immunonological cells. It has also been suggested that by the induction of Fas receptor and ligand expression at the surface of treated cancer cells, an autocrine, paracrine or fratricidal death may follow. Since the cells express both the receptor and the ligand, there may be cross-linking between the receptor and the ligand of the same cell (autocrine), or the receptor on one cell and the ligand of another cell (paracrine). Different teams of researchers have demonstrated that chemotherapy-induced apoptosis involves the activation of the caspase-3 and -8 regardless of whether the cell is of type I or type II. It is suggested that in the type I cells, two apoptosis initiation pathways are used during chemotherapy. Therefore, the treatment favors Fas receptor aggregation, which causes the activation of the caspase-8, which in turn will directly activate the caspase-3, the caspase-8 may also activate the Bid protein by cleaving it and Bid will then activate the mitochondrial apoptotic pathways. For type II cells, apoptosis is controlled by a mitochondrial pathway since the use of FADD inhibitors did not decrease chemotherapy-induced apoptosis this type of cells. Therefore, caspase-8 activation in type II cells occurs after the signalling events in the mitochondrion.

Other studies have shown that DNA damage caused by chemotherapy or by irradiation increases the death receptor DR5 expression in a p53-dependant and independent manner.

We can observe the involvement of many proteins following a chemotherapy treatment. It is important to understand the mechanisms used for this treatment since different cancers develop different tricks to avoid death.

6 Lactic Acid Bacteria

It is the scientist E. Metchnikoff (1845-1919) who proposed that the longevity and the health of the Bulgarian people is attributable to their ingestion of fermented milk products. It was well known that certain bacteria are pathogenic to the organism; thus, it was proposed that these bacteria be substituted by yogurt bacteria since they had long been used without fear. Many characteristics exist in order to define the good lactic acid bacteria: they must conserve their activity and their viability prior to consumption, they must survive the gastrointestinal tract, they must be able to survive and to proliferate in the intestines, and must eventually produce beneficial effects. In addition, the micro-organisms must not be pathological nor toxic.

Since then, many trials have been conducted in order to improve the state of health by modification of the intestinal flora through living lactic acid bacteria. Today, the beneficial effects of these lactic acid bacteria are well identified and there are attempts to explain the mechanism(s) related to such benefits. Salminen's team has summarized the most important beneficial effects, supported by scientific evidence such as immunological modulation and reinforcement of the intestinal mucous barrier. Other teams have demonstrated that, in the mouse, cancer growth and metastases may be inhibited by the *Lactobacillus casei* strain of bacteria. Different mechanisms are proposed in order to explain to what such benefits would be due: the modification of the intestinal flora, adherence to the intestinal mucous membrane with the capacity of preventing the adherence of pathogenic bacteria or the activation of pathogens, the modification of food proteins by intestinal microflora, the modification of bacterial enzymatic capacity, especially those suggested relating to the induction of cancer, and finally the influence on the permeability of intestinal mucosa.

Most of the studies indicate a therapeutic potential of lactic acid bacteria and yogurt which is mainly due to the change in grastro-intestinal micro-ecology. The efficiency of lactic acid bacteria is enhanced by their capacity of adherence to the intestinal wall since the adherent bacterial strains have a competitive advantage, important to maintain their place in the gastrointestinal tract. On the other hand, no bacterial strain has yet been shown to adhere in a permanent fashion. By increasing the quantity of lactic acid bacteria in the intestines, it is possible to eliminate growth of pathogenic bacteria which in turn will contribute to a reduction of infections. An intact intestinal epithelium with an optimal intestinal flora represents a barrier against invasions or colonisation by pathogenic micro-organisms, antigens and harmful compounds for the intestinal tract.

In general, the consumption of lactic acid bacteria acts by a reinforcement of the non-specific immune response or acts as an adjuvant in the antigen-specific immune response. Studies on animals have demonstrated that the lymphoid tissue associated to the intestines is stimulated by living lactic acid bacteria, resulting in a production of cytokines and antibodies (IgA) and an increase of mitogenic activity of the cells forming Peyer plaques and splenocytes. In the studies on human cells, the production of cytokine, phagocytic activity, antibody production, function of T cells and NK cell activity are increased by the consumption of yogurt or when the cells are exposed to lactic acid bacteria in a in vitro.

Certain evidences indicate that the yogurt stimulating the immune system may be associated with the reduction of pathological incidences like cancer, gastrointestinal disorders and allergy symptoms.

6.1 Anti-Cancerous Properties

The lactic acid bacteria would have antineoplastic properties in a variety of cancer cellular strains of human and animal origin. In brief, the lactic acid bacteria reduce the viability of tumoral cells, reduce carcinogenesis induced in the colon and in the liver, inhibits mutagenic activity and binds to potentially mutagenic compounds. Although no mechanism is known, it is suggested that the inactivation or the inhibition of cancer formation in the intestinal tract is induced.

There exists considerable interest for the metabolic activity of the intestinal microflora, especially in relation to colon cancer etiology. Studies have been conducted amongst others on the measure of key enzymes: $\beta$-glucoronidase, azo-reductase, and nitro-reductase. These enzymes catalyze the conversion of indirect carcinogens into carcinogens in the intestines. By the absorption of lactic acid bacteria, these would reduce the activity of these key enzymes and would thus prevent the formation of tumors. An oral supplement of lactic acid bacteria (*L. acidophilus*) of human origin causes a significant reduction of these three key enzymes. These results have been partially confirmed by the Marteau team which recorded a reduction only in nitro-reductase in 9 of the subjects that had ingested lactic acid bacteria (*L. acidophilus, B. bifidium*) during 3 weeks. The studies have continued on an animal colon cancer model chemically induced by 1,2-dimethylhydrazine dihydrochloride (DMH). DMH activation occurs in the large intestine and it is the bacterial enzyme $\beta$-glucoronidase which transforms it into a potential carcinogen. The suppression of this enzyme can reduce the activation of DMH and subsequently tumor formation. These studies show that the addition of lactic acid bacteria can delay the formation of colon cancer by prolonging induction, indicating that the *lactobacilli* can slow tumor development in the animal experimental model.

In summary, many conclusions are suggested related to the inhibitory functions of lactic acid bacteria towards colon cancer. Besides, the increase or the stimulation of immune functions could contribute in reducing the risk of the development or the reappearance of the cancer. Also, lactic acid bacteria could take the place of pathogenic bacteria which would be at the origin of the formation of mutagenic compounds causing colon cancer.

There is therefore a need to find more efficient methods or methods having less secondary effects than the treatments already available for treating the disease.

SUMMARY OF THE INVENTION

As mentioned here above, new properties of these bacteria have been discovered. Indeed, it has been discovered surprisingly that the effect of lactic acid bacteria, in particular those contained in the product sold under the trade name Bio-K+ International, in combination with an anticancer agent can cause cellular apoptosis.

Many mechanisms can be at the origin of such phenomenon. For example, lactic acid bacteria can avoid the mutation that is at the origin of cancers. It can also prevent the progression of tumors by reinforcing the immune system.

The Applicant has discovered surprisingly that the use of lactic acid bacteria would have as an effect to prevent cancer formation, in particular, colon cancer.

The Applicant has also discovered surprisingly that the use of lactic acid bacteria in combination with an anticancer agent has the effect of increasing the susceptibility of cancerous cells to apoptosis.

Thus, the present invention concerns the use of at least one lactic acid bacteria strain to reinforce an immune response in a mammal in order to prevent or to treat a cancer.

Another object is the use of at least one lactic acid bacteria strain to facilitate the induction of apoptosis in cancer cells.

Another object is the use of at least one lactic acid bacteria strain for the manufacture of a drug destined for the treatment or the prevention of cancer.

According to a preferred embodiment, the bacterial strain is in a live or irradiated form. More particularly, this bacterial strain is of the genus *Lactobacillus* and more preferably of the species *Lactobacillus acidophilus* such as the strain I-1492 filed at the CNCM and/or *Lactobacillus casei*.

Another object of the present invention is to provide a composition to treat or to prevent a cancer, such as colon cancer. The composition of the present invention comprises an efficient quantity of at least one lactic acid bacterial strain such as previously and an acceptable pharmaceutical carrier. According to a preferred embodiment of the invention, the composition also comprises an anticancer agent, such as 5-fluorouracil.

According to another object, the present invention proposes a method to prevent or to treat a cancer in a mammal, characterized in that it comprises the administration in said mammal of a composition such as previously defined.

Another object of the present invention concerns the use of lactic acid bacteria to increase apoptosis of cancerous cell.

Another object of the present invention concerns the use in combination of lactic acid bacteria and an anticancer agent, such as 5FU for the treatment of a colon cancer.

Another object of the invention is to provide a kit to prevent or to treat a cancer in a mammal, characterized in that it includes a container containing a composition such as the one previously defined.

BRIEF DESCRIPTION OF THE DRAWINGS

FIG. 12a illustrates the cells not having been subjected to any treatment. FIG. 12b illustrates cells in the presence of 5FU in a concentration of 100 µg/ml. FIG. 12c illustrates cells in the presence of lactic acid bacteria at a concentration of $10^8$. FIG. 12d illustrates the combination of cells, lactic acid bacteria ($10^8$) and of 5FU (100 µg/ml).

DETAILED DESCRIPTION OF THE INVENTION

Figure 1:
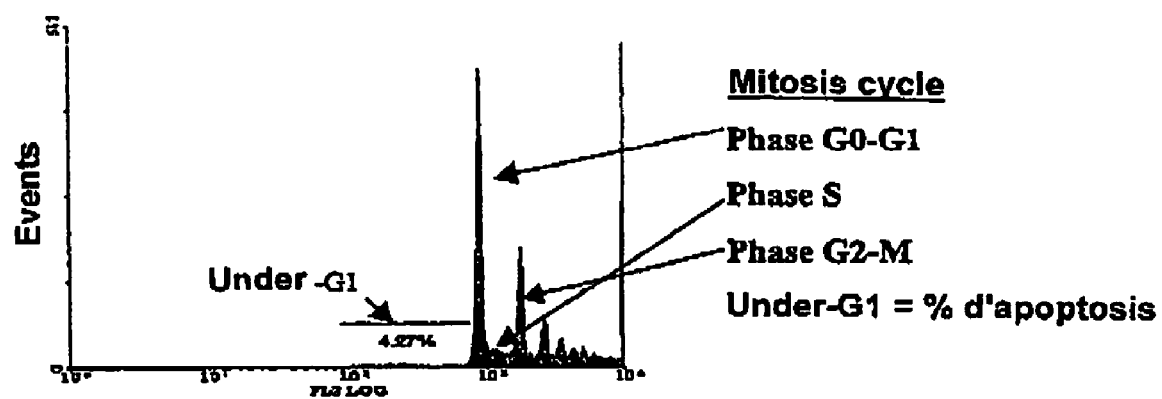
FIG. 1 is a diagram illustrating a typical analysis of the percentage of apoptosis by flow cytometry.
Figure 2:
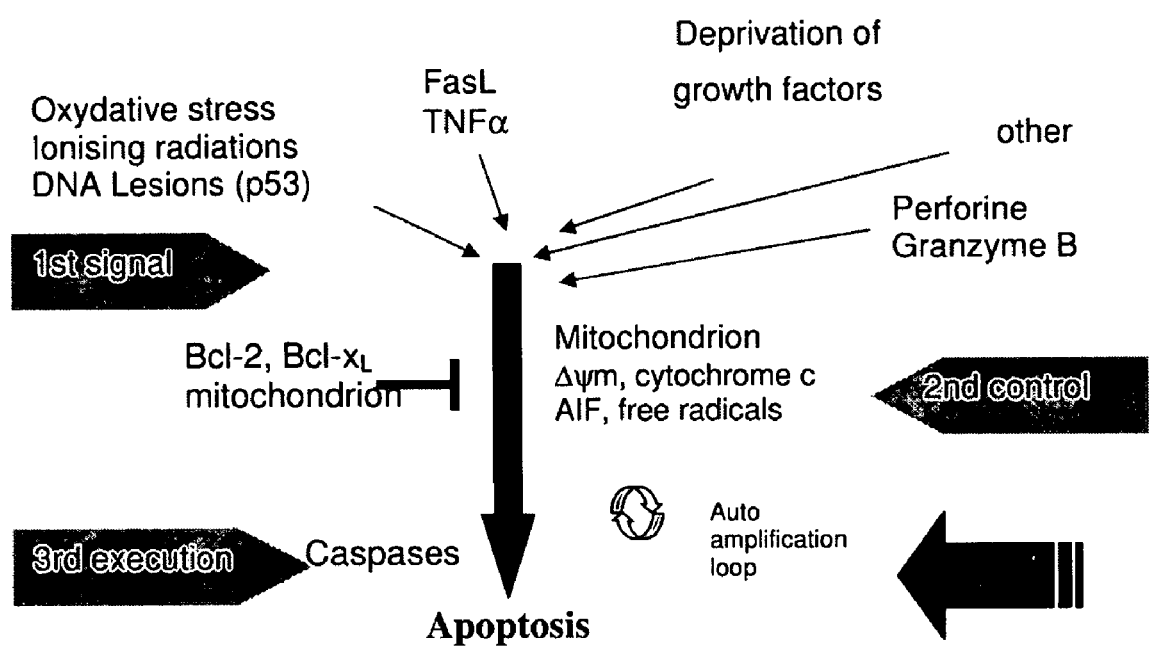
FIG. 2 is a diagram illustrating a model of the apoptotic process.
Figure 3:
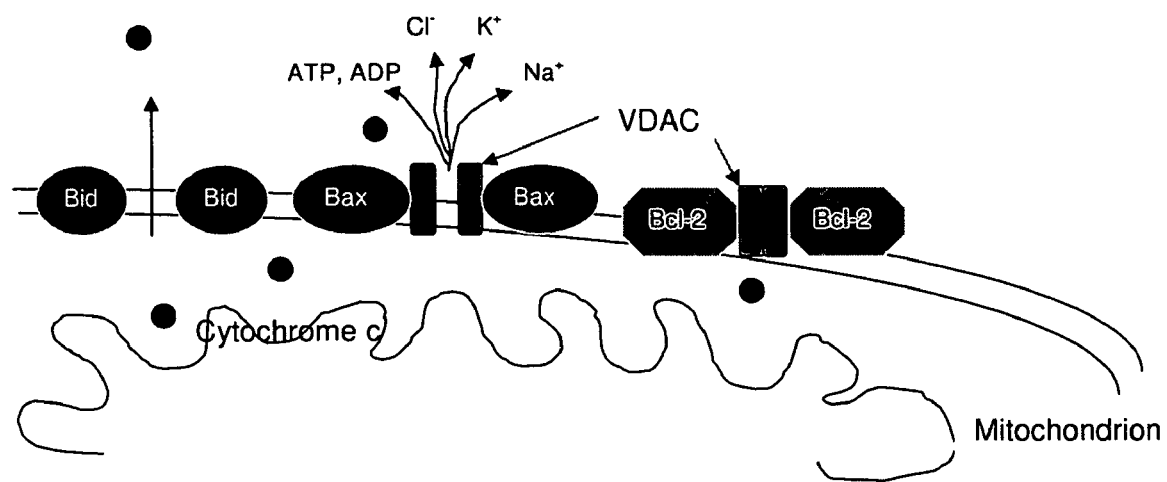
FIG. 3 is a diagram illustrating the hypotheses of release by the Bcl-2 protein family.
Figure 4:
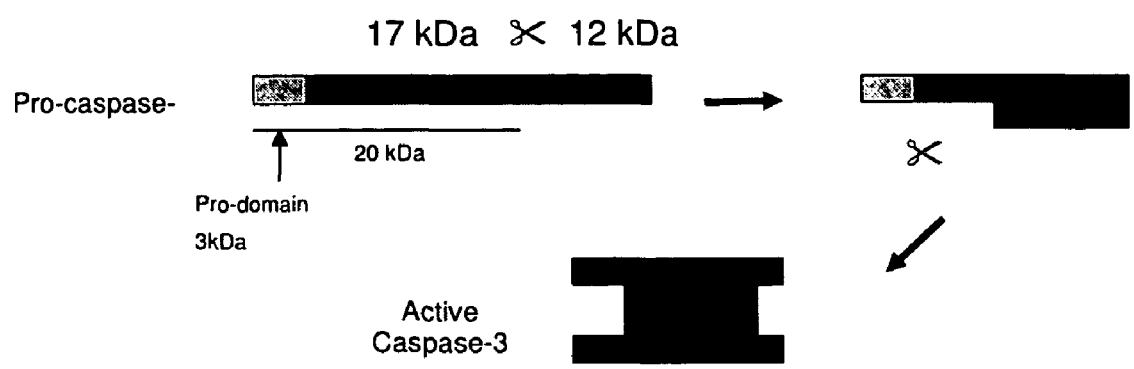
FIG. 4 is a diagram illustrating the proteolytic maturation of pro-caspase-3.
Figure 5:
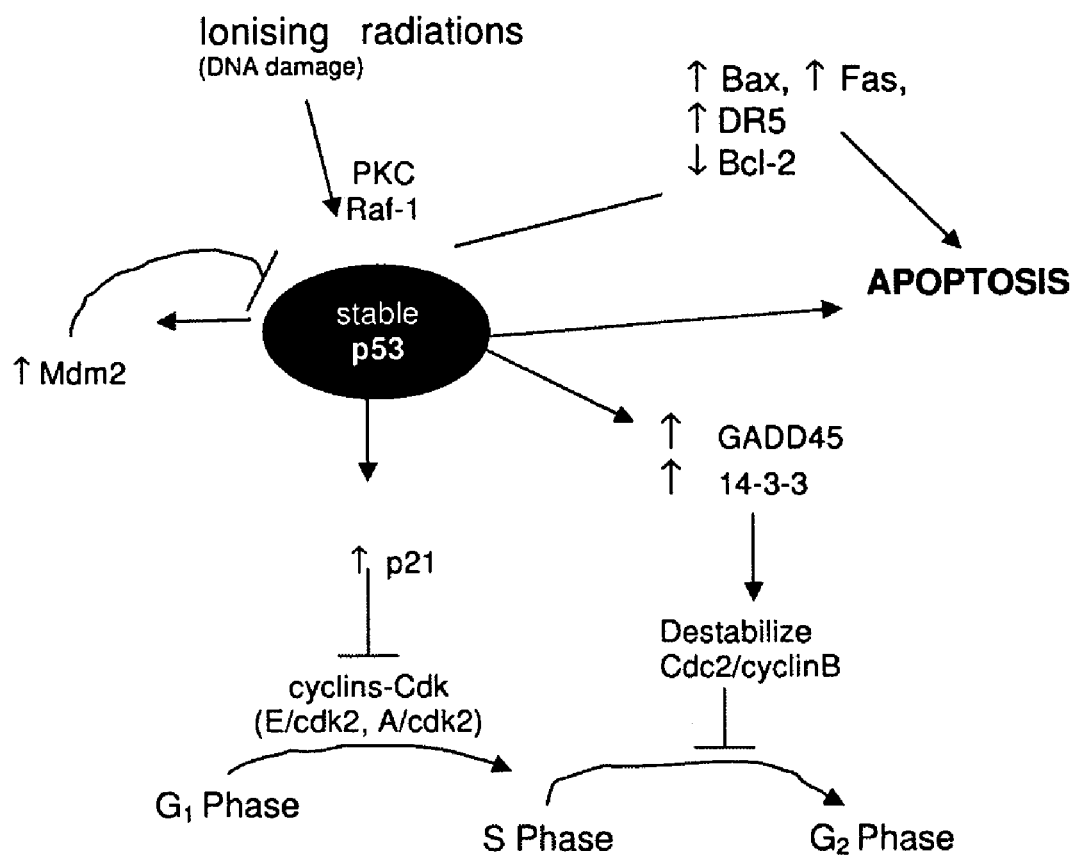
FIG. 5 is a diagram illustrating the recapitulation of the effects of p53 activation.
Figure 6:
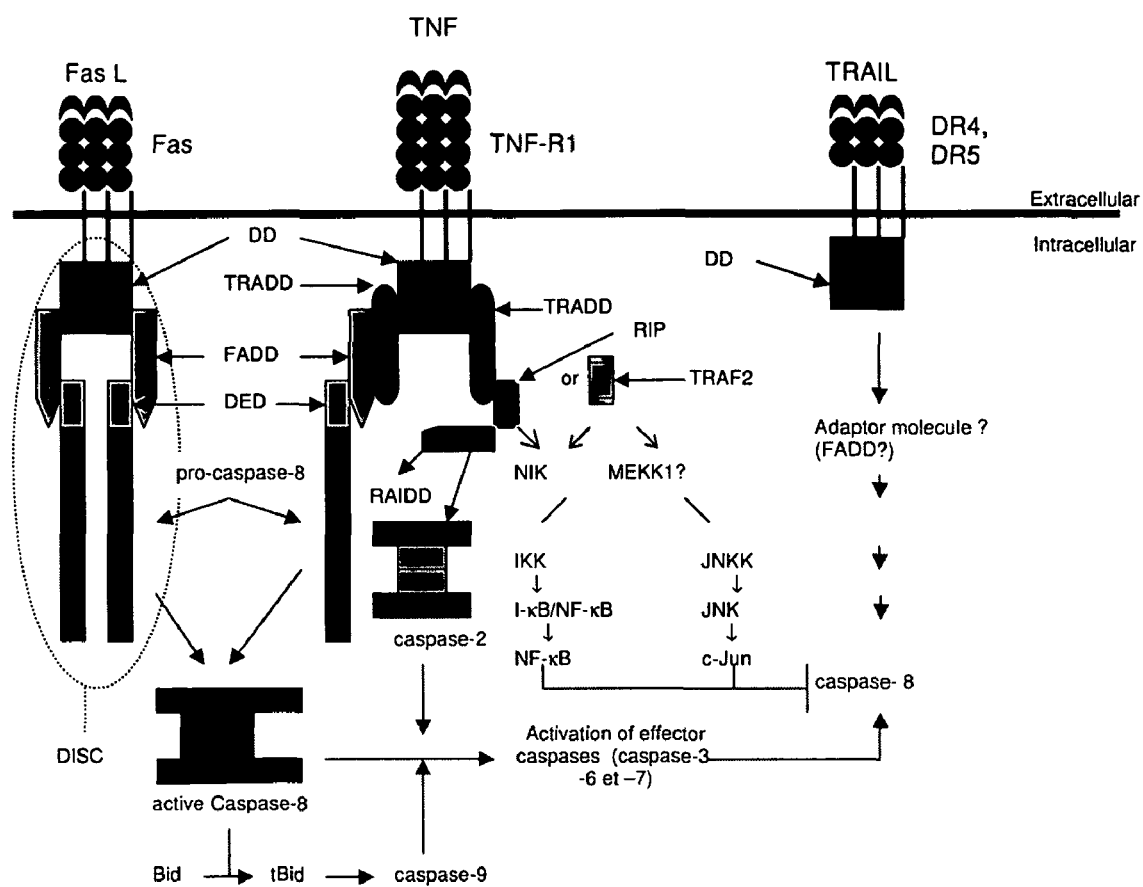
FIG. 6 is a diagram illustrating the structure of membranous death receptor members and their interaction with the main cytoplasmic effectors involved in apoptotic pathways.
Figure 7:
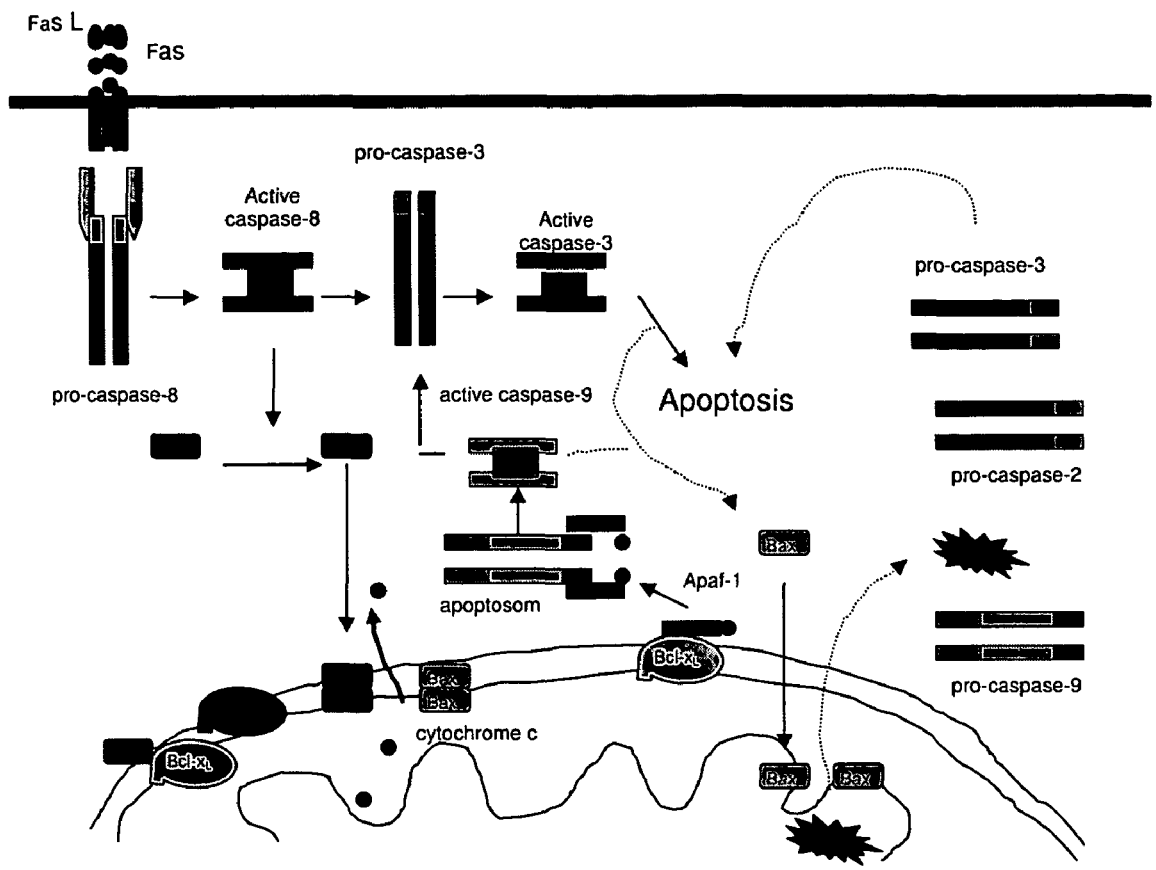
FIG. 7 is a diagram illustrating the interconnections between two different apoptotic transduction pathways.

The present invention therefore concerns the highlighting of the use of new properties of lactic acid bacteria strains in the prevention or the treatment of a cancer. More particularly, the use of these lactic acid bacteria aims to facilitate the induction of cellular apoptosis of a cancer.

The invention also concerns the implication of said lactic acid bacterial strains in methods and useful compositions in the treatment or the prevention of a cancer, such as colon cancer.

According to a first embodiment, the present invention aims at the use of lactic acid bacterial strains to strengthen the immune response in a mammal in order to prevent or treat a cancer.

According to a second embodiment, the present invention aims for the use of lactic acid bacteria to facilitate the induction of apoptosis in cancer cells. By "facilitate the induction of apoptosis", we mean a process by which the presence of lactic acid bacterial strains of the invention positively modulates cellular death of a tumor, and preferably a tumor of the colon.

By "mammal", we mean any living organism which may be subject to a cancer, and this includes vertebrate beings such as in particular human beings and domestic and wild animals.

By "treat", we mean a process by which the symptoms of cancer, and particularly that of the colon, are reduced or completely eliminated.

By "prevent", we mean a process by which the cancer, and particularly that of the colon, is controlled or delayed.

According to a preferred embodiment of the invention, the bacterial strain is of the genus *Lactobacillus* and preferentially in a living or irradiated form. More particularly, the bacterial strain is of the species *Lactobacillus acidophilus* or *Lactobacillus casei*. In the case where the species chosen is *Lactobacillus acidophilus*, the inventors prefer advantageously to use the I-1492 strain deposited at the CNCM.

According to a third embodiment, the present invention in regarding the use of these lactic acid bacterial strains for the preparation of compositions useful in the treatment or the prevention of cancer, such as colon cancer. A composition according to the present invention comprises an efficient quantity of at least one lactic acid bacterial strain and one acceptable pharmaceutical vehicle. Preferably, the composition of the invention includes a mixture of *L. acidophilus* and *L. casei* strains.

By "pharmaceutically acceptable", we understand a vehicle that can be administered without risk to a mammal, in particular to a human being, and this with little or no negative or toxic secondary effects. Such a vehicle can be used for different functions. For example, it can be used as a preservation, solubilizing, stabilizing, emulsifying, softening, coloring, odoring agent, or as an antioxydant agent. These types of vehicles may be easily prepared by using methods well known by a person in the art.

According to a preferred embodiment, the composition of the present invention comprises, besides, an anticancer agent. To this effect, any anticancer agent that could be useful in the present context is included within the scope of the present invention However, 5-fluorouracil is advantageously used as an anticancer agent. The composition of the present invention can also be part of a more complex therapeutic formulation which is useful in the treatment and the prevention of cancer.

According to a fourth embodiment, the invention proposes a method to prevent or to treat a cancer, in particular a colon cancer, in a mammal. According to another closely related embodiment, the present invention proposes a method to facilitate apoptosis of cells of a cancer in a mammal, such as a human. These methods include, amongst others, the stage of administering to said mammal a composition according to the present invention.

The quantity or the concentration of lactic acid bacteria that is administered to a human or to an animal or that is present in the composition of the invention is a therapeutically effective quantity. A therapeutically effective quantity of lactic acid bacteria is the quantity necessary to obtain positive results without causing excessively negative secondary effects in the host to which the lactic acid bacteria or the composition is administered. Moreover, an efficient quantity of lactic acid bacteria to treat a particular cancer is a quantity which is sufficient to attenuate or to reduce in any fashion the symptoms linked to cancer. Such a quantity can be administered in a single dose or can be administered according to a regime, by which it is efficient. The quantity of lactic acid bacteria according to the present invention can treat the cancer but, typically, it is administered in order to attenuate the symptoms of cancer. The exact quantity of lactic acid bacteria or each of the components of the composition to be administered will vary according to factors such as the type of cancer to be treated, the other ingredients in the composition, the method of administration, the age and the weight of the mammal, etc. . . .

The compositions according to the present invention can be presented in any solid or liquid form that is usual to pharmaceutical administration, that is for example for liquid administration forms, in a gel, or any other support known by a person skilled in the art. Among the compositions that are used, we can in particular cite compositions that can be administered orally. In the present case, the composition of the invention can be administered in the form of food or food supplements. We can also cite injectable compositions more specifically destined for injections in the blood circulation of humans.

A person versed in the art will know how to prepare compositions that are pharmaceutically acceptable and determine, in function of many factors, the privileged method of administration and the quantity that should be administered. Among the factors that can influence his choices we find: the nature of the treatment, the exact nature of the ingredients, active or not, entering in the composition; the stage of the disease; the condition, the age and the weight of the patient, etc.

The present invention also includes useful pharmaceutical kits, for example, for the prevention or the treatment of a cancer, such as colon cancer. The kits comprise one or many containers further containing a composition according to the present invention. Such kits can also include, if desired, one or many conventional pharmaceutical components like, for example, containers containing one or many pharmaceutically acceptable vehicles, or any other additional component, which will be obvious to a person skilled in the art. A kit according to the present invention can advantageously include instructions in pamphlet form or on any other printed support, indicating the quantities of the components to be administered, the instructions for administration, and/or the instructions to mix the components.

The example here after will allow to highlight other characteristics and advantages of the present invention.

EXAMPLE

The following example serves to illustrate the scope of the use of the present invention and not to limit its scope. Modifications and variations may be made to it without going away from the spirit nor the scope of the invention. Eventhough one may use other methods or products equivalent to those that we find hereinafter to test or to carry out the present invention, the material and the preferred methods are described.

Introduction

In the context of the present invention, in order to determine how the lactic acid bacteria help in the apoptosis of cancer, trials have been conducted on the human colon cancer cell line LS-513. The lactic acid bacteria used constitute a mixture of *Lactobacillus acidophilus* and *Lactibacillus casei*. The anticancer agent is 5 fluorouracil (5FU). This compound acts as an inhibitor of the enzyme that synthesizes thymine.

Material and Methods

1 Lactic Acid Bacteria 1.1 Origin

The mixture of bacteria used for the different experiments is supplied by the company Bio-K (Laval, P.Q. Canada). The mixture comprises a combination of *Lactobacillus acidophilus* I-1492, which is the subject of the international application no. PCT/CA97/00915, and of *Lactobacillus casei*.

1.2 Preparation

The bacteria received in 9 mL of MRS complex medium (Difco Laboratories, Detroit, USA) are immediately multiplied in 100 mL of the same medium by taking 100 µL of the bacterial suspension. After an incubation of 18 hours in an incubator at 37° C., 10 mL of glycerol is added to the 100 mL mixture which is then divided into 1 mL aliquots in many sterile plastic flasks that can contain 1.5 mL. These flasks are stored in a freezer at −80° C.

For the different stimulation protocols, a flask is thawed and put into 9 mL of MRS and incubated for 18 hours at 37° C. After this incubation period, a subculture is done. A volume of 100 µL is taken and added to 9 mL of MRS which is also incubated for 18 hours at 37° C. After these incubations, the bacteria are washed twice in sterile PBS and collected by centrifugation at 3500 RPM during 10 minutes. They are then suspended in a final volume of 9 mL of sterile RPMI containing 10% foetal bovine serum and are then ready to be used for a cellular stimulation. During the different experiments, the bacteria are used in a heated, irradiated and live form.

1.3 Heating

The bacteria are heated for 40 seconds at "high" in a microwave oven (General Electric, Turntable Microwave Oven, 700 Watt) in order to obtain a 100° C. temperature and to produce the mixture of bacteria which will be used as heated bacteria. This step occurs in a closed glass container.

1.4 Irradiation

In order to produce the mixture of irradiated bacteria, the tubes of live bacteria are irradiated at a minimal dose to obtain a 100% mortality, i.e. 5kGy. The mixtures are irradiated in a Gammacell-220 (MDS, Nordion, Laval, P.Q., Canada) using Cobalt-60 ($^{60}$Co) as a gamma ray emitting source.

In order to do a bacterial count to obtain a concentration of bacteria per 1 mL of this suspension is added to 9 mL of peptoned water, an isotonic solution containing 0.1% of bactopeptone (Difco Laboratories, Detroit, USA). Serial dilutions are made. Then, 1 mL of these dilutions is taken and put in a Petri dish to which one adds 10 mL of MRS to 1.5% agar (Difco Laboratories, Detroit, USA) to allow a counting after a 48 hour incubation in an incubator at 37° C. Each sample is done in duplicate.

2 Cancer Cells 2.1 Origin

The LS 513 cell line (ATCC, Rockville, Md., USA) is a continuous colon cancer line of human origin.

2.2 Culture

The cell line being adherent, one must detach the cells with the help of a trypsin-EDTA solution (Gibco, Burlington, ON, Canada) in order to resuspend them in RPMI supplemented with L-glutamine and 10% FBS which we can thus call "complete RPMI". The plates are done the day before the stimulation to allow the cells to adhere to the plates. The day of the stimulation, the different products are added at the desired concentrations and then the cells are incubated during a determined period for each type of experiment, in an incubator at 37° C., 5% $CO_2$ and saturated in humidity.

3 Co-Cultures of Cancer Cells and Bacteria 3.1 Addition of Bacteria

Once the culture plates are ready to be used, that is when the cells have had time to adhere, and the bacteria ready to be used, the latter added according to the stimulation protocol in wells containing the adherent cells and the "complete RPMI" medium. An incubation is done during a given time based on the experiment to conduct.

3.2 Experiment Involving the Addition of Butyrate

The plate of cancer cells containing $3 \times 10^5$ cells per well is incubated overnight to allow the cells to adhere. Then, the different concentrations of butyric acid (Sigma, St-Louis, USA) are added to the wells containing the adherent cells and the culture medium, the complete RPMI. After this addition, a 48 hour incubation is done in order to measure the percentage of apoptosis according to the technique described hereinafter.

3.3 Collecting and Studies of Supernatants

The goal of this experiment is to verify if the presence of bacteria modifies the pharmacological presentation of 5FU. The first stimulation is made on adherent cells for a period of 48 hours in the presence of the different stimulation products. Following this incubation, the supernatants are collected and added onto a new culture of freshly adherent cells. Then, a second incubation of 48 hours is done then the cells are harvested and the percentage of apoptosis is measured.

4 Measures of the Vialibity of Cancer Cells 4.1 Proliferation 4.1.1 MTT

The cells are prepared as described above. The test is done in a 96-well plate. A volume of 100 µL of a concentration of $3.3 \times 10^5$ cells per mL is deposited in each well, except in the first row which will serve as a "blank". Once the stimulation products are added, an incubation of 48 hours is made. Following the incubation, the supernatants are removed by aspiration, and the cellular sheet is washed, by delicately adding 200 µL of PBS in each well, and by rapidly decanting the added PBS in the sink. Then, a solution of MTT (Sigma, St-Louis, USA) 5× diluted in complete RPMI is added to the wells and an incubation of 5 hours at 37° C. is done. Then, the solution is decanted and another solution is added with the goal of dissolving the crystals formed in the live cells. This solution is composed of 50% of dimethyl formamide and 12% sodium dodecyl sulfate (SDS). An incubation of 18 hours is required to dissolve all the crystals. Following this incubation, the plate is read in a spectrophotometer (Mandel Scientific Company, Bio-Tek Instruments, Microplate EL309 Autoreader) at 540 nM. Each sample is made in triplicate, and the obtained values are averaged. The average value of the standard is the "100%" of living cells. In order to obtain the percentage of other samples, it suffices to do a cross product.

4.2 Apoptosis 4.2.1 Flow Cytometry

A concentration of $5 \times 10^4$ cells per mL, with 6 mL per well, is used in order to obtain $3 \times 10^5$ cells per sample. The cells are prepared as indicated above. The different products are added to the wells, and an incubation of 48 hours is done.

Following the incubation, the supernatants of the cells are collected in different 15 mL tubes and centrifuged at 1500 RPM during 5 minutes. The cellular pellets are then collected by decantation of the supernatant and put on ice. This stage consists in recuperating the cells in suspension. Afterwards, the adherent cellular sheet is washed with 0.5 mL trypsin-EDTA, then 0.2 mL trypsin-EDTA is added to each well to allow the cells to detach when they are incubated for around 8 minutes in the incubator at 37° C. The cells are suspended in 3 mL of complete RPMI 10% FCS to stop the enzymatic activity of trypsin. The cellular suspension is centrifuged at 1500 RPM for 5 minutes in the tubes used for flow cytometry. Afterwards, the two cellular pellets (cells in suspension and adherent cells) are combined and washed twice with cold PBS supplemented with 0.25% EDTA in order to avoid the formation of agglomerates of cells. Following the washings, 0.5 mL of propidium iodide solution is added to the cellular pellet. The solution is composed of 0.1% sodium citrate (Fisher Scientific, New Jersey, USA), 0.1% de TritonX-100 (Sigma, St-Louis, USA), 50 µg/mL of RNase (Sigma, St-Louis, USA) and of 20 µg/mL of propidium iodide (Sigma, St-Louis, USA). A 15 minute incubation at 4° C. is done to then analyse the samples by flow cytometry (Coulter Epics XL-MCL). FIG. 1 summarizes a typical result from a flow cytometry analysis. Different peaks are formed due to the differences in fluorescence existing between each phase of the cellular cycle. The more the content of intact DNA is high, the more the fluorescence is high and vice-versa. The program measures the percentage of fluorescence that the large spike forms under the corresponding spike of G0-G1, this spike represents pieces of fragmented DNA, consequence of the cleavage of DNA by different enzymes activated during apoptosis.

5 Measure of the Expression of the Proteins Involved in Apoptosis (p53, p21, Caspase 3, Bax)

5.1 Western Blotting 5.1.1 Protein Stimulation and Extraction

A total of around $6 \times 10^5$ cells per sample are used. The following day, when the cells have become adherent, the stimulation products are added. The different stimulation products are 5-fluorouracil (100 µg/mL) and the bacteria, live or heated, at a concentration of $1 \times 10^8$ bacteria par mL. These products will bring the cells to become apoptotic by the modulation of different proteins involved in the process. It is this modulation, increase in expression or protein activation, that the technique allows to verify. Following different stimulation times (since it concerns kinetics), the cells are collected and centrifuged at 1500 RPM for 5 minutes. Then, 50 µL of lysis buffer composed of 50 mM Tris-HCl pH 7.5, NaCl 150 mM, Nonidet P-40 1% (Roche Diagnostics, Laval, P.Q.) as well as a Complete™ pill (containing protease inhibitors) (Roche Diagnostics, Laval, P.Q.), are added to the cellular pellet which is then incubated 30 minutes on ice. The volume of 50 µL is collected and put into a 1.5 mL micro-tube. A centrifugation of 10 minutes at 15 000 RPM is done in order to precipitate the cellular debris. The supernatant is collected and an equal volume of "sample buffer" is added. The "sample buffer" is composed of 100 mM Tris-HCl pH6.8, 2% SDS, 20% glycerol and of 0.006% of bromophenol blue. At the end, the samples are aliquoted by volume of 20 µL and are stored at a temperature of −20° C.

5.1.2 Protein Separation and Identification

The samples of protein are separated on a polyacrylamide-SDS gel at 4% and 12% using the "mini-PROTEAN" machine from Bio-Rad. The proteins migrate within an electrical current of 200 volts during 45 minutes. The migration occurs in an "electrode buffer" at pH 8.3 composed of 1.5% Tris-Base, of 7.2% glycine and of 0.5% SDS in mili-Q water. Afterwards, the proteins are transferred on a "Hybond ECL" nitrocellulose membrane (Amersham Pharmacia Biotech Inc., Baie d'Urfé, Quebec) with the help of the Bio-Rad transfer machine during one hour at 100 volts in a transfer buffer composed of 0.58% Tris-Base, of 0.29% glycine, of 0.037% SDS and of 20% methanol. Following the transfer, the membrane is "blocked" with a blocking solution composed of 0.1% PBS-Tween 80 at 0.1%, as well as 5% powdered skimmed milk for one hour at room temperature with agitation. Then, the first labelling is done with the antibody recognizing the targeted protein. The antibody is diluted in the blocking solution according to a concentration given by the provider. After one hour of labelling, a 15 min. washing is done followed by two washings of 5 minutes with the blocking solution. The second labelling is done with a second antibody which recognizes the first antibody and which is coupled to the peroxidase. A one hour incubation is done with this second antibody which is also diluted in the blocking solution at a concentration given by the provider. As soon as this incubation is finished, a 15 minute washing, as well as two 5 minute washings, are done with a solution of 0.1% PBS-Tween 80 without powdered skimmed milk. In order to detect the different proteins, an ECL solution (Amersham Pharmacia Biotech Inc, Baie d'Urfé, P.Q., Canada), which leads to the activation of the peroxidase, is added to the membrane according to the instructions of the provider. Afterwards, the labellings are revealed on photographic paper (hyperfilm ECL, Amersham Pharmacia Biotech Inc., Baie d'Urfé, P.Q., Canada) which will be labelled by the activated peroxidase. The photographic paper is then developed. Table 1 summarizes the proteins targeted and the reactants used.

TABLE 1

The antibodies used for the different proteins to be identified.

| Protein | Description | Dilution | Company |
|---|---|---|---|
| Primary Antibody | | | |
| p53 | Purified human anti-p53 | 1:1000 | BD PharMingen, Mississauga, Ontario |
| | Iso type: mouse $IgG_{2a}$ | | |
| p21 | Purified mouse anti-p21 | 2:1000 | BD PharMingen, Mississauga, Ontario |

TABLE 1-continued

The antibodies used for the different proteins to be identified.

| Protein | Description | Dilution | Company |
|---|---|---|---|
| Caspase 3 | Iso type: mouse IgG$_1$ Anti-caspase 3 rabbit polyclonal | 1:1000 | BD PharMingen, Mississauga, Ontario |
| Bax | Anti-Bax | 1:1000 | Santa Cruz California, USA |
| Secondary Antibody | | | |
| IgG | Mouse anti-IgG Coupled to peroxidase Developed in goat | 3:10000 | Sigma, St-Louis, USA |
| IgG | Rabbit anti-IgG Coupled to peroxidase Developed in goat | 2.5:10000 | Sigma, St-Louis, USA |

6 Measure of the Expression of Markers on the Cellular Membrane (Fas, Fas L)

6.1 Flow Cytometry

A total of about 5×10$^5$ cells is used per sample. The cells are prepared as mentioned previously. A 24 hour incubation is done after the addition of different stimulation products (5FU, live or heated bacteria and others according to the experiments that are conducted).

Following the incubation, the cellular sheets are washed with 0.5 mL of trypsin-EDTA, then 0.2 mL trypsin-EDTA is added to the cellular sheets, which are then placed in the incubator at 37° C. for 10 minutes. Once the cells are detached, 3 mL of complete RPMI are added, and the cellular suspension is then centrifuged during 5 minutes at 1500 RPM. The supernatants are decanted and the cells are placed on ice. Then, 20 µL of the antibody solution against the Fas receptor (BD PharMingen, Mississauga, Ontario) or Fas ligand (BD PharMingen, Mississauge, Ontario) are added to the cellular pellet to which 50 µL of "flow cytometry buffer" composed of 1×PBS, 1% BSA, 0.02% sodium azide and 0.25% EDTA were previously added. An incubation of half an hour on ice in the dark is required. Then, two washings with 4 mL of "flow cytometry buffer" are done, by centrifugation at 1,500 RPM during 5 minutes. To the cells labelled with the Fas ligand antibody, a quantity of 0.25 µL per tube of streptavidine-PE (BD PharMingen, Mississauga, Ontario) is added, following the first incubation and the two washings. A second incubation is done for 30 minutes in the dark, followed by two other washes. At the end of a labelling, 250 µL of paraformaldehyde solution (1×PBS, 2% paraformaldehyde) and 250 µL of "flow cytometry buffer" are added in order to fix the labellings. The tubes are wrapped in aluminium paper and placed at 4° C. until the analysis of the samples.

7 Measure of the Expression of the Nurr77 Gene

7.1 RNA Extraction

3×10$^5$ cells are used per sample. A 3 hour incubation is done following the addition of the different stimulation products. The cells are then collected with the help of a scraper, and centrifuged at 1500 RPM for 5 minutes. The total RNA of each sample is removed and purified by using the High Pure RNA kit from Roche Diagnostics (Laval, P.Q., Canada) as instructed by the manufacturer. The concentration of RNA is then measured with the machine (Pharmacia Biotech, Gene Quant RNA/DNA Calculator), then adjusted to 92 ηg/µL.

7.2 RT-PCR

The LightCycler RNA amplification SYBR Green 1 kit from Roche Diagnostics (Laval, P.Q., Canada) is used in order to accomplish the reverse transcription reaction (RT) and the polymerase chain reaction (PCR). The LightCycler principle is very similar to that of the Thermocycler. The major difference consists in the possibility, with the LightCycler, of observing the amplification at each cycle, thanks to a fluorescent molecule called SYBR Green 1 which inserts itself into each double strand formed. The more double strands formed, the more fluorescence is observed with the help of the program included with the LightCycler. The two reactions, RT-PCR, are done in a capillary specially constructed for the LightCycler (Roche, Laval, P.Q., Canada) and it is sufficient to make a single mixture of the products contained in the kit and to use this ensemble according to the instructions of the manufacturer.

Before doing an amplification, it is necessary to finalize certain conditions. For example, the concentration of MgCl$_2$, the temperatures and the time. An ideal concentration of MgCl$_2$ is to be determined. For the present amplification, a concentration of 7 mM proved to be the best. The concentration of the primers is 0.5 mM, as suggested by the manufacturer. In the case of the Nurr77 gene, the primer sequence used for the positive strand is 5'-CGACCCCCTGACCCCT-GAGTT-3' (SEQ. ID. NO: 1) and the one for the negative strand is 5'-GCCCTCAAGGTGTTGGAGAAGT-5' (SEQ. ID. NO: 2) (Kang, J-H, Biol. Pharm. Bull.) The amplification by these primers gives 658 base-pairs. The programming of the LightCycler machine is described in the instruction manual provided by the manufacturer. Two other parameters vary in the amplification program: amongst others in the hybridization segment, the temperature it uses varies according to the primers. The temperature (fixed at 5° C. less than the hybridization temperature of the primers (Tm) is calculated by the following formula: Tm=2° C. (A+T)+4° C. (C+G). For the primers used, the Tm is 64° C. The second parameter is the incubation time for the elongation, always found in the amplification program; it is determined by the following formula t=(number of base pairs from the amplified product÷25) seconds. In our case, the number of bases being 658, we thus obtain 26 seconds. Following the 35 cycles necessary to amplify the wanted part of the gene, a point of fusion curve is made, using a temperature of 10° C. above the hybridization temperature. Therefore, the amplifications are subject to a progressive increase of the temperature and at each degree the fluorescence is measures and registered. By increasing the temperature in a progressive fashion, the double strands formed detach when the temperature becomes high enough, and it is thus at this temperature that a decrease in fluorescence is observed. The program makes a fusion point curve with the registered fluorescences and, afterwards, it measures the derivative of the fluorescence in function of the temperature. By knowing the theoretical fusion temperature of the amplification product, it is possible to obtain the value of the area below the curve of the spike peak formed by the separation of the strands of the amplification product at this temperature. Since the machine does not allow to visualise the number of amplified base pairs, a migration on a 2% agarose gel with a base pair marker allows the verification following staining with ethium bromide coloration at a concentration of 0.5 µg/mL for 15 minutes.

8 Treatments with PKC Inhibitors or Stimulators

The stimulations made with the PKC inhibitors and stimulators are accomplished in the same way the stimulations by bacteria and by 5FU. First of all, the cells are prepared the day before to allow them to adhere, and the day of the stimulation, the different stimulation products are added at the same time as the GÖ 6976 (Sigma) inhibitor and/or the PKC stimulators, ionomycine (Sigma) and PMA (phorbol 12-myristate 13-acetate) (Sigma). Then, a 48 hour incubation is done, the cells are collected and the percentage of apoptosis is measured.

9 Cytokine Dosage 9.1 TNF Dosage by Bioassay

It is possible to measure out the quantity of TNF in a supernatant with the help of the L929 cell line which is a mouse fibroblast line sensitive to the cytotoxic action of TNF. The principle of this bioassay is simple: the more TNF there is in the supernatant added to the L929 cellular sheet, the more cellular death will occur. We can then measure the rate of the remaining live cells. First, the cells are cultured in complete RPMI 1640+5% FCS. The cells detach themselves from the flask with the help of trypsin-EDTA (Gibco, Burlington, ON, Canada) by incubating around 1 minute at 37° C. A cellular count is done to prepare a suspension of $3.3 \times 10^5$ cells/mL for the bioassay.

A volume of 75 μL is deposited in each well of a 96-well plate. All the lines receive this volume except the first which is used as an empty control. Following a 24 hour incubation, a volume of 25 μL of actinomycin D at a 2 μg/mL concentration is added to all the wells of all the lines, except the second line which serves as a control of actinomycin D and this in order to stop cellular growth. Then, the different samples are added starting from the fourth line with 100 μL per well, and this in triplicate. The third line stays empty since it will serve as a positive control, i.e. it will represent the maximum number of cells since there is no cytotoxic agent added. With the added samples, successive dilutions are made from the 100 μL that are diluted in series in the 8 following rows. When the samples are diluted, they are incubated from 16 to 20 hours at 37° C.+5% $CO_2$. After this incubation, the supernatants are disposed of and the cells are fixed to the bottom of the well with the help of a 5% formaldehyde solution with 100 μL per well for 5 minutes. Then, the plates are emptied and rinsed 3 times with running water. The cells that have remained fixed are then dyed with crystal violet with 50 μL per well for 5 minutes. Afterwards, the plates are emptied and the excess dye is eliminated by 3 rinses with running water. Once the plates have dried well, 100 μL of 33% acetic acid solution is added to each well to dissolve the crystal violet absorbed by the fixed cells. The absorbency is read at a wave length of 540 nm in a plate spectrophotometer, using column 1 as a reference ("Blank").

In order to calculate the number of TNF units, we consider a unit of TNF corresponding to the inverse of the dilution factor giving 50% cytotoxicity. In order to calculate the percentage of cytotoxicity for each sample, the following equation is used.

$$\% \text{ cytoxicity} = \frac{O.D. \text{ sample}}{O.D. \text{ positive}} \times 100$$

Therefore, the O.D. of the sample is the average of the three absorbencies obtained for a dilution following the reading of the plates. The O.D. of the positive control is the average of the wells of line 3. The % cytotoxicity is calculated for each dilution. Afterwards, a linear regression curve is plotted for the dilutions of a sample, the dilution factor (=x) and the % cytotoxicity (=y) and the 50% point is found with the help of the equation for the curve. The inverse of the dilution ($2^x$) is equivalent to the number of units of TNF in the initial non diluted sample. The results are expressed in U/mL.

Results

1) Search for the Optimal Dose of 5-Fluorouracil

Figure 8:
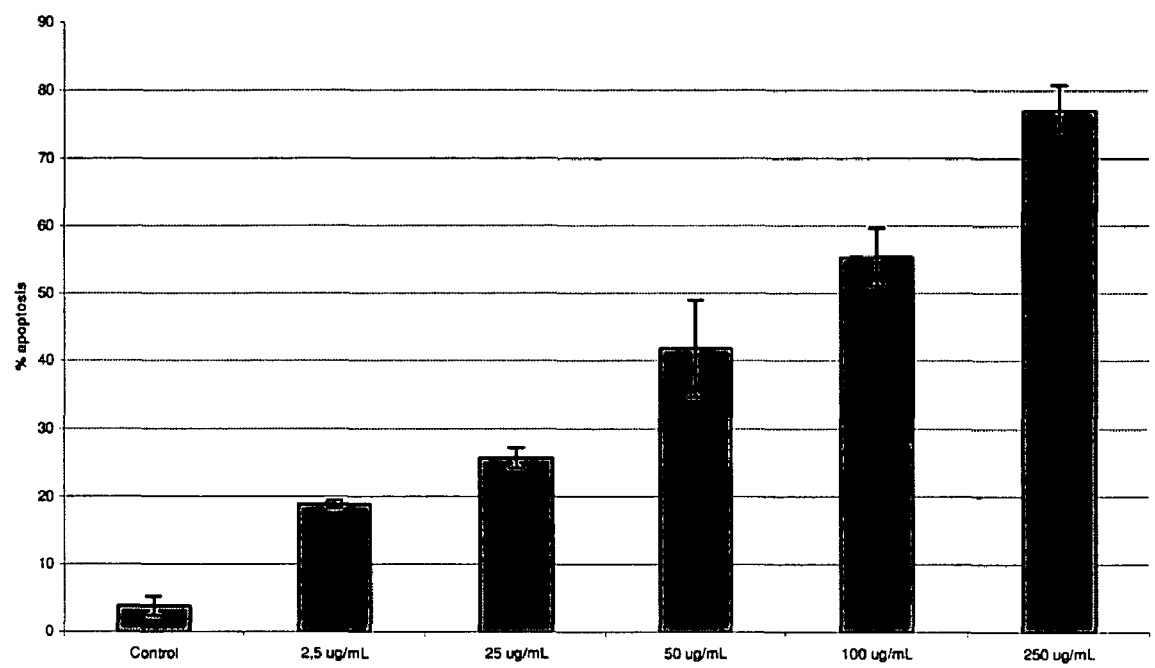
FIG. 8 is a graph showing the optimal dose of 5-fluorouracil to obtain 50% of cellular death.

FIG. 8 shows the measure of apoptosis by flow cytometry following exposure to increasing doses of 5-fluorouracil (5FU) in order to obtain an ideal concentration yielding 50% mortality. A total of $3 \times 10^5$ cells is put in the presence of different concentration of 5FU during 48 hours. Then, the DNA content of the cells is labelled with propidium iodide and analysed by flow cytometry in order to obtain the percentage of apoptosis. The following results are the average of two independent experiments.

Figure 9:
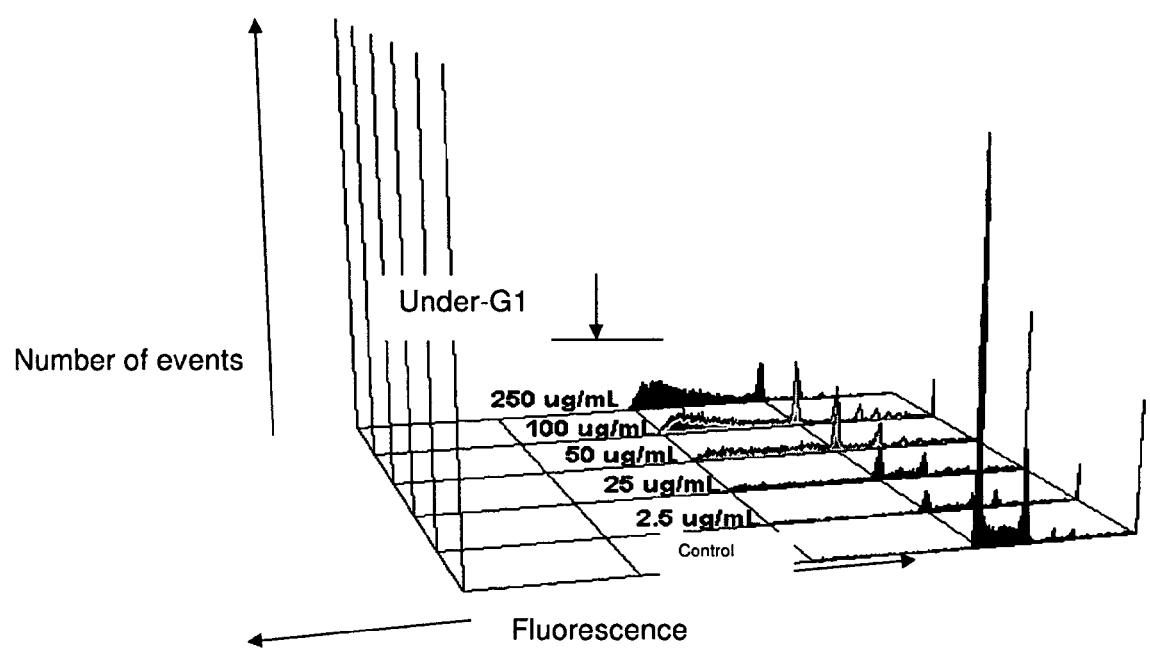
FIG. 9 shows a visual presentation of diagrams of apoptosis obtained by flow cytometry.

FIG. 9 illustrates a diagram representing one of the two experiments conducted in order to obtain the ideal concentration of 5FU. The machine measures the number of events under the G1 peak in relation to the number of events of the sample which yields a percentage result. Since we know that the events under G1 corresponds to cleaved DNA, sign of apoptosis, we thus attribute this percentage as the value of apoptosis.

Figure 10:
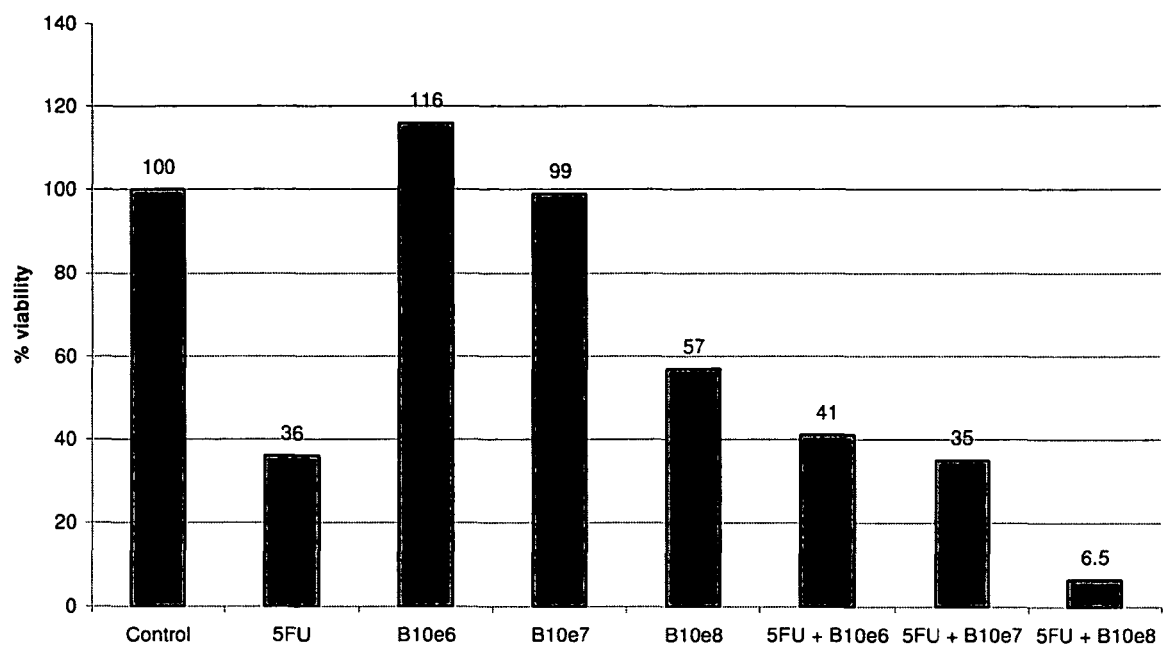
FIG. 10 is a graph showing the effect of the composition according to a preferred embodiment of the invention on LS 513 cell viability.

2) Action of the Combination of 5-fluorouracil and Live Bacteria on the Viability of LS 513 Cells FIG. 10 illustrates the viability of colon cancer cells and dosed by MTT after an incubation of 48 hours in the presence or absence of 5-fluorouracil (5FU) (2.5 μg/mL) and of live bacteria (B) at different concentrations ($10^6$-$10^8$). A total of $3.3 \times 10^4$ cells per well in a 96-well plate is put into contact with the different stimulation products. The coloration produced by the MTT reaction with the live cells is evaluated on a spectrophotometer at a wave length of 540 nm. Each sample is the average of 3 different wells.

Figure 11:
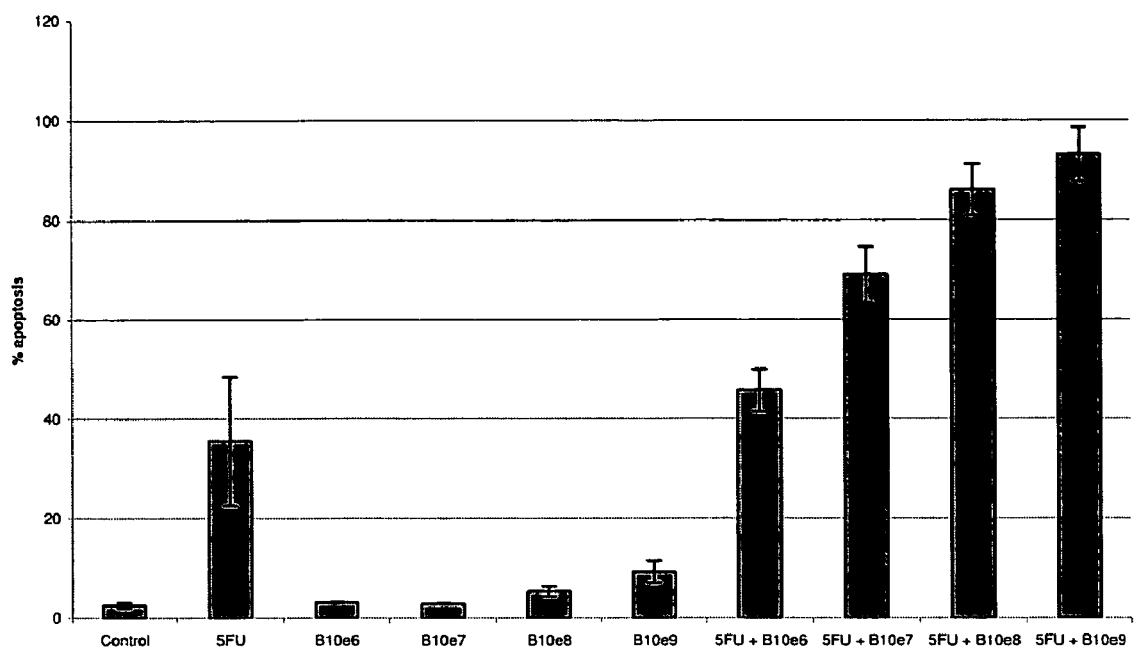
FIG. 11 is a graph showing the effect of the composition according to a preferred embodiment of the invention on LS 513 cell apoptosis.

FIG. 11 illustrates the effect of live bacteria and of 5FU on the apoptosis of LS 513. Live lactic acid bacteria (B) at different concentrations ($10^6$-$10^8$) and of 5-fluorouracil (5FU) (100 μg/mL) are added to the LS 513 cells. The measure of apoptosis by flow cytometry is done following an incubation of 48 hours. The labelling of DNA with a propidium iodide solution allows to observe the percentage of cells having cleaved DNA (under-G1) produced following incubation. The control is cells without treatment.

Figure 12:
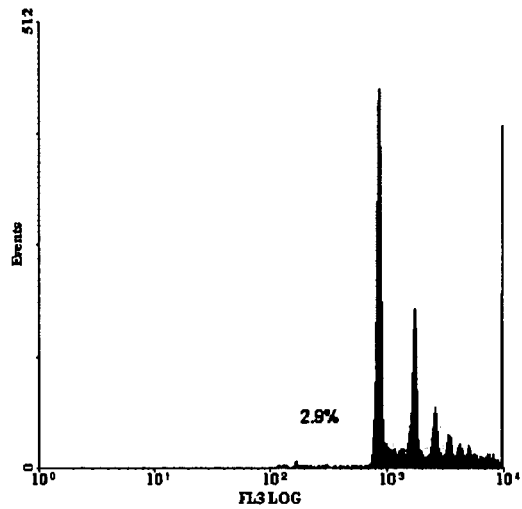
FIGS. 12a, 12b, 12c, and 12d are diagrams illustrating the measure for apoptosis by flow cytometry.
Figure 12:
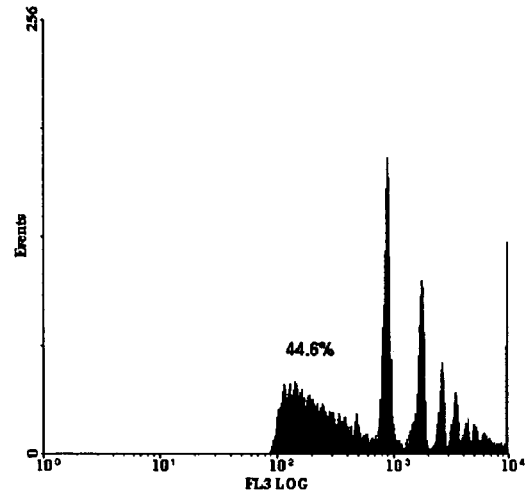
Figure 12:
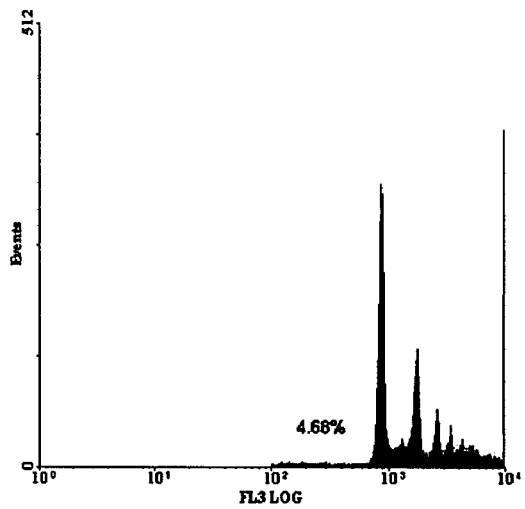
Figure 12:
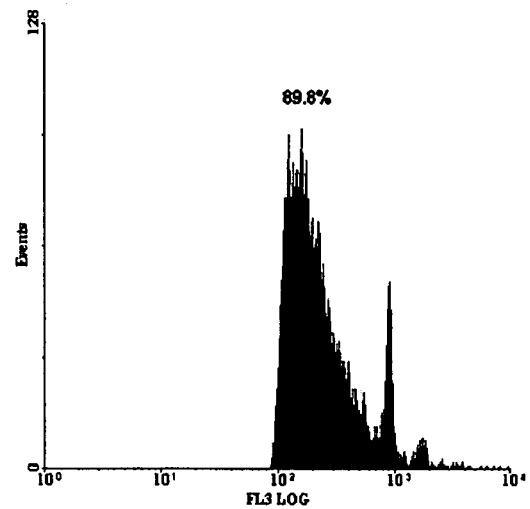

FIG. 12 shows examples of flow cytometry diagrams to measure apoptosis. These 4 diagrams represent 4 different samples produced during an experiment. The number of events under G1 gives a percentage in relation to the rest of the stages of the mitotic cycle. The control (A) being the cells without treatment, image B is composed of cells put in the presence of 5FU at a concentration of 100 μg/mL, image C is that where live bacteria at a concentration of $10^8$ were combined to the cells, and the last image (D) represents the combination of cells, of live bacteria ($10^8$) and of 5FU (100 μg/mL).

Figure 13:
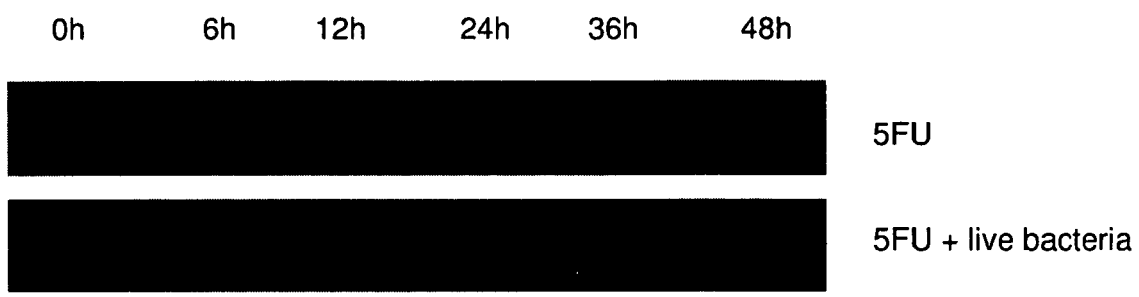
FIG. 13 shows a Western blot illustrating the activation of caspase-3 by the cells in the presence of a composition according to a preferred embodiment of the invention.

FIG. 13 illustrates a Western blot of caspase 3 and this in its pro-active form. An incubation of 48 hours in the presence of live bacteria at a concentration of $10^8$ and of 5-fluorouracil (5FU) at a concentration of 100 ng/mL was done. From this incubation, the proteins were removed and migrated on a polyacrylamide gel. Afterwards, they were transferred to a nitrocellulose membrane and labelled with a specific antibody for caspase 3 and this at a concentration of 1:1000.

Figure 14:
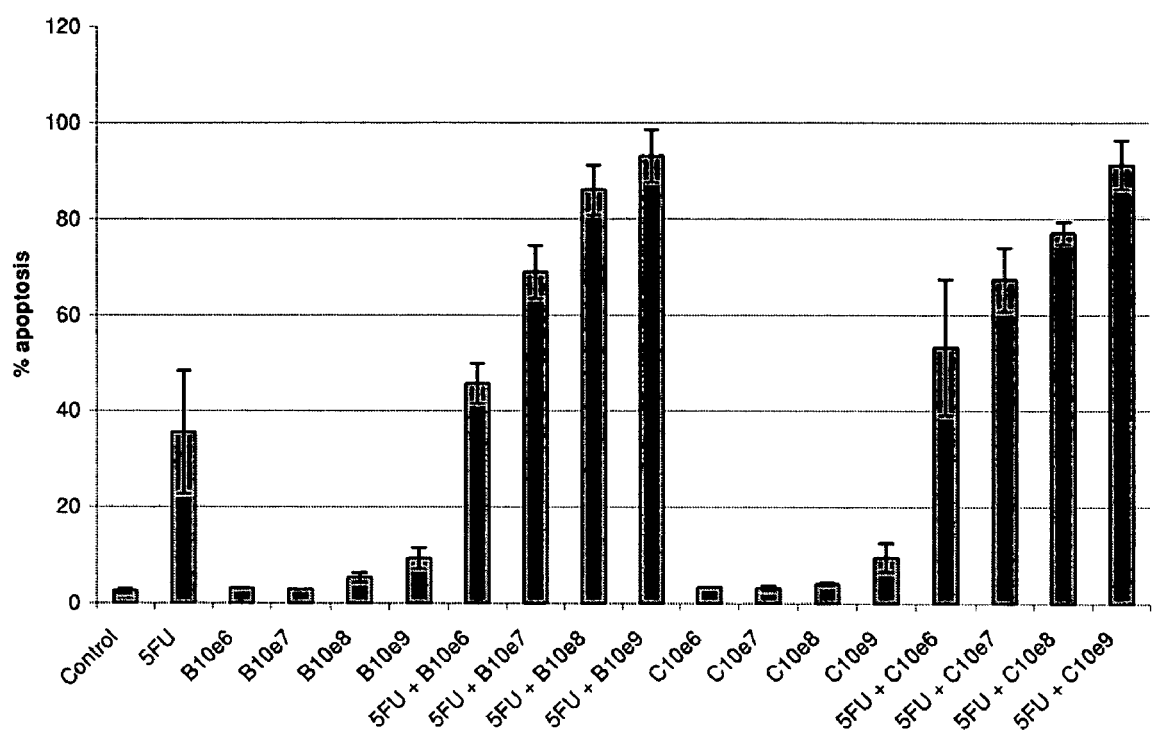
FIG. 14 is a graph showing a measure of apoptosis of LS 513 cells in the presence of compositions according to a preferred embodiment of the invention.

3) Action of the State of the Bacteria 3.1) Live Bacteria versus Irradiated Bacteria FIG. 14 shows the measure of LS 513 cellular apoptosis in presence of live bacteria, irradiated bacteria and 5FU. This figure shows more specifically the measure of apoptosis by flow cytometry by the percentage under G1 with the help of a propidium iodide label (20 μg/mL). The colon cancer cells are put in the presence or absence of 5-fluorouracil (5FU) (100 μg/mL) and of living bacteria (B) or of irradiated bacteria (C) at different concentrations ($10^6$-$10^9$) and this for a period of 48 hours. The controls are cells without treatment.

3.2) Live Bacteria versus Heated Bacteria

Figure 15:
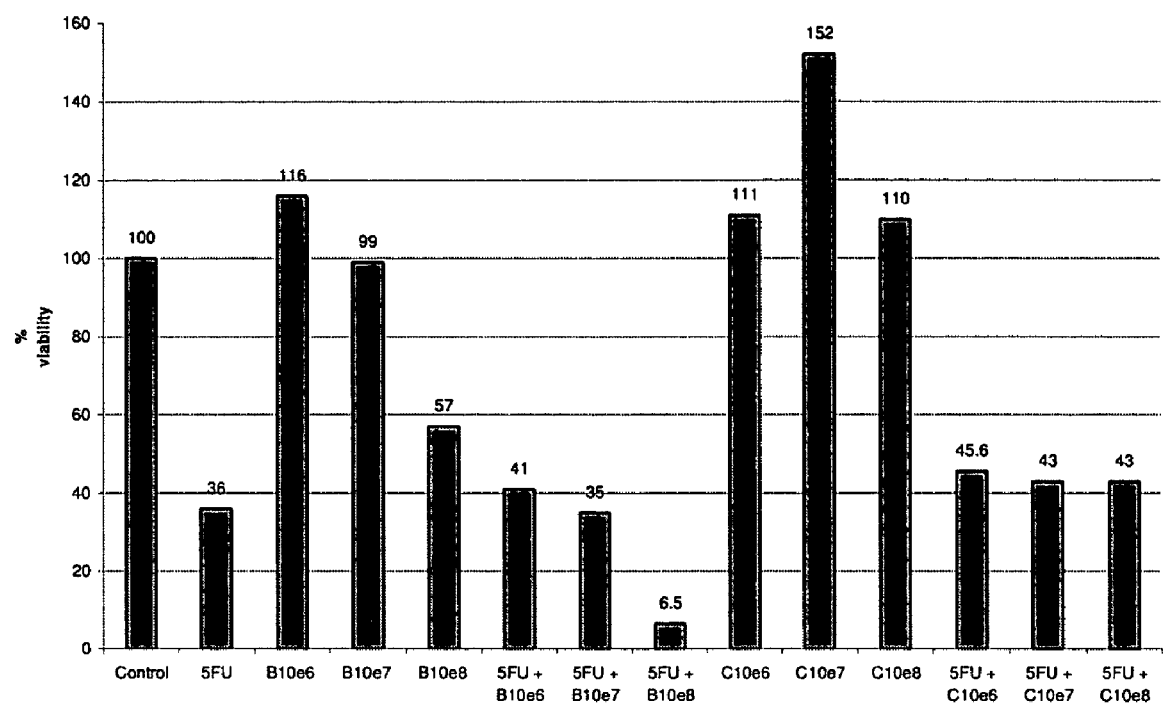
FIG. 15 is a graph showing the effect of the viability of LS 513 cells by MTT.

FIG. 15 shows the measure of the viability of LS 513 cells by MTT. More particularly, this Figure shows the effect of live bacteria (B) and of heated bacteria (C) at different concentrations (10eX) in presence or absence of 5-fluorouracil (5FU) (A)(2.5 μg/mL) on the viability of LS 513 after an incubation of 48 hours. These values are obtained by spectrophotometer reading (540 nm), by the coloration due to MTT which stains the functional mitochondria thus only those of the living cells. The cellular concentration used is $3.3 \times 10^4$ cells per well. The following results are the average of three wells of a 96-well plate.

Figure 16:
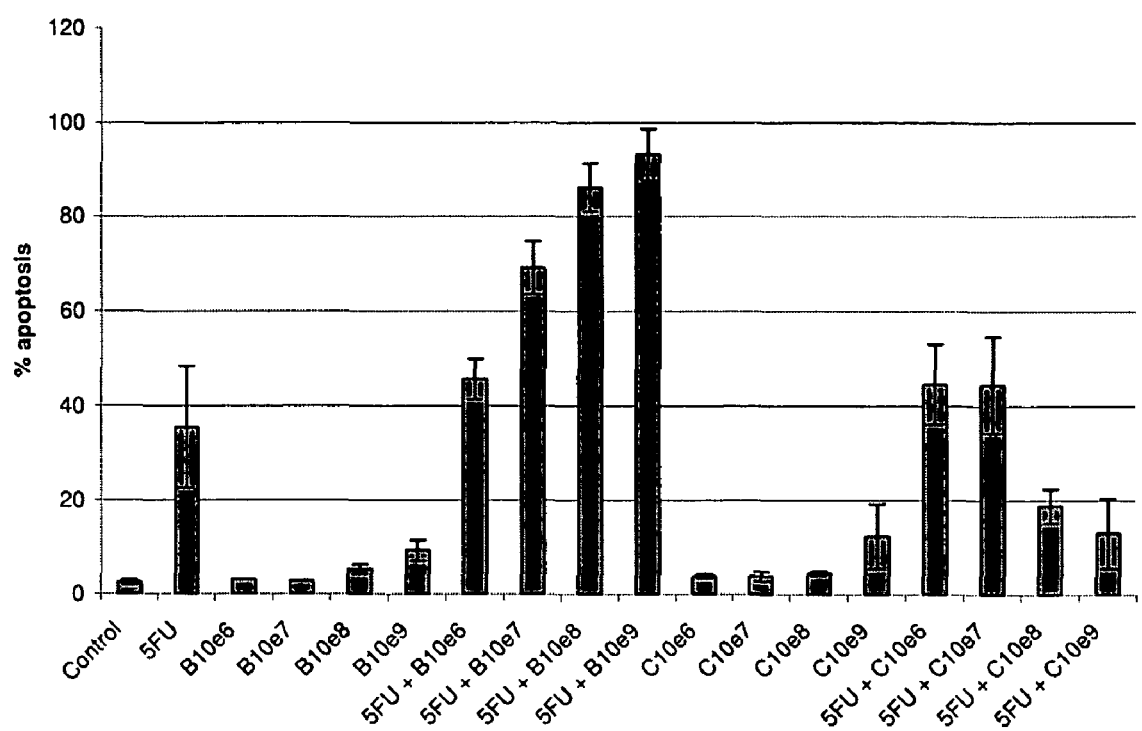
FIG. 16 is a graph showing the effect of live lactic acid bacteria versus heated lactic acid bacteria on LS 513 cell apoptosis.

FIG. 16 shows the effect of live bacteria versus the heated bacteria on the apoptosis of LS 513 cells. The analysis of the percentage under G1 by DNA labelling was obtained with propidium iodide. A total of 10 000 events are treated per sample. An incubation of 48 hours in presence of live bacteria (B) and of heated bacteria (C) and this at different concentrations with or without 5-fluorouracil (100 μg/ml) are the different samples illustrated in the figure.

Figure 17:
FIG. 17 shows Western blots showing the effect of living lactic acid bacteria versus heated lactic acid bacteria on the activation of caspase-3.

FIG. 17 shows the effect of live or heated bacteria on caspase 3 activation.

4) Possible Mechanisms Inherent to Bacterial Cultures

Figure 18:
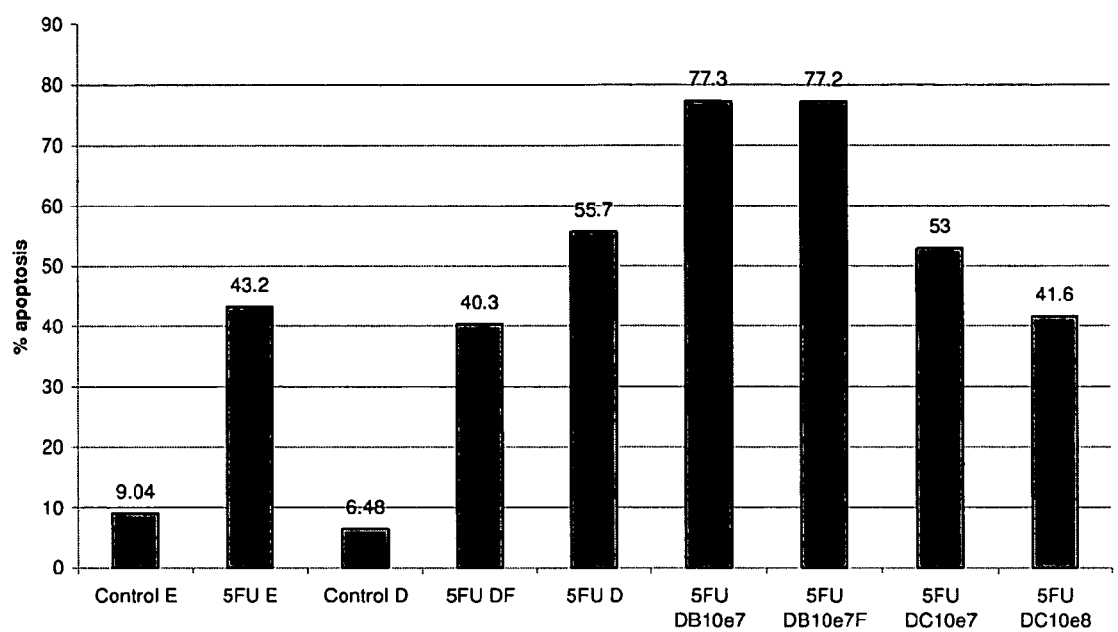
FIG. 18 is a graph showing the measure of inherent apoptosis in lactic acid bacterial strains of the present invention.

FIG. 18 shows the measure of apoptosis inherent to strains of lactic acid bacteria of the invention. A first stimulation was made during 48 hours. Certain wells did not contain any cells (F). The different supernatants (D) were collected and added on a fresh cellular culture (E). The concentration of 5-fluorouracil (5FU) is of 100 μg/mL and two different concentrations are used for the living bacteria (B) and the heated bacteria (C) which are $1 \times 10^7$ and $10^8$. The measure of apoptosis is done by flow cytometry by DNA labelling with propidium iodide.

Figure 19:
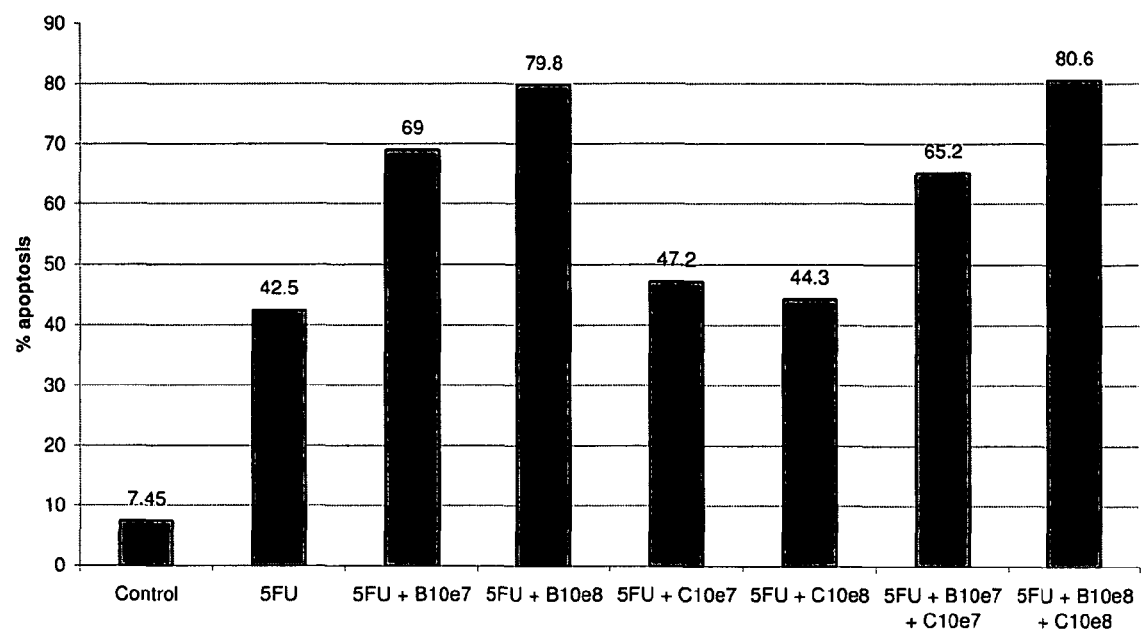
FIG. 19 is a graph showing the apoptotic effect of the mixture of living bacteria and of heated bacteria.

FIG. 19 shows the apoptotic effect of the mixture of live bacteria and heated bacteria. The measure of apoptosis by flow cytometry was taken after an incubation of 48 hours. The LS 513 cell line is put in the presence of a given concentration of 5FU (100 μg/mL) as well as in the presence of live bacteria (B) and of heated bacteria (C) at two different concentrations (107 and 108). The control is composed of cells without treatment.

Figure 20:
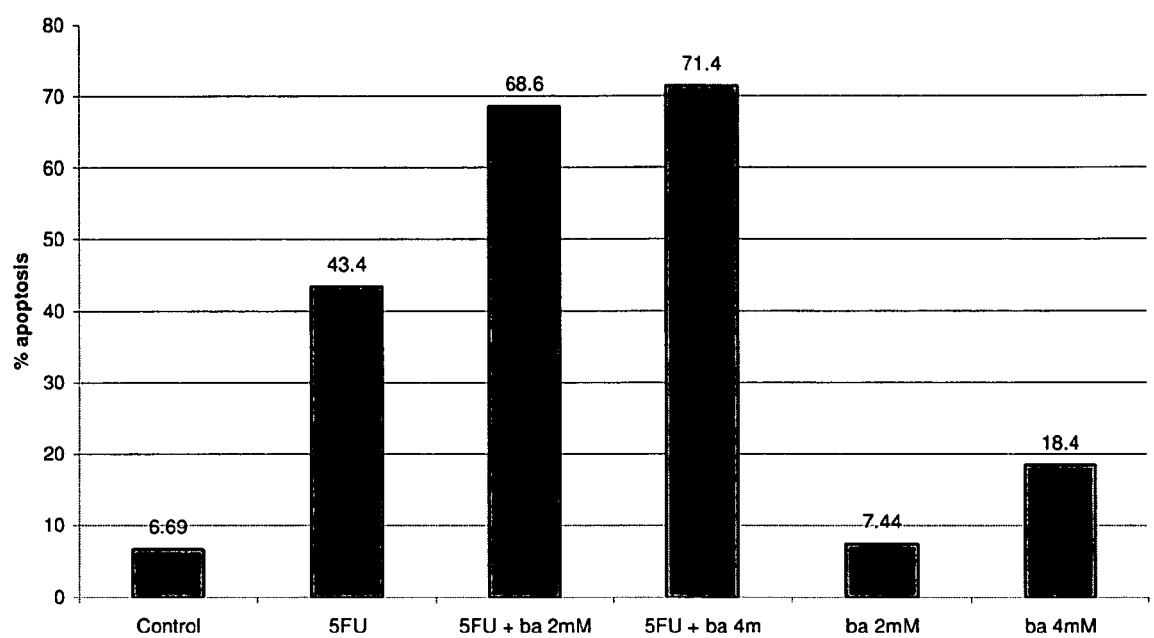
FIG. 20 is a graph showing the effect of the addition of butyric acid and of 5FU on LS 513 cell apoptosis.

FIG. 20 shows the effect of adding butyric acid and 5FU on LS 513 cellular apoptosis. A dose of 5FU (100 μg/mL) as well as different doses (2 mM and 4 mM) of butyric acid (ba) are added to the cancerous colon cells. Apoptosis is measures after a 48 hour incubation.

5) Possible Mechanism Inherent to Tumor Cells

Figure 21:
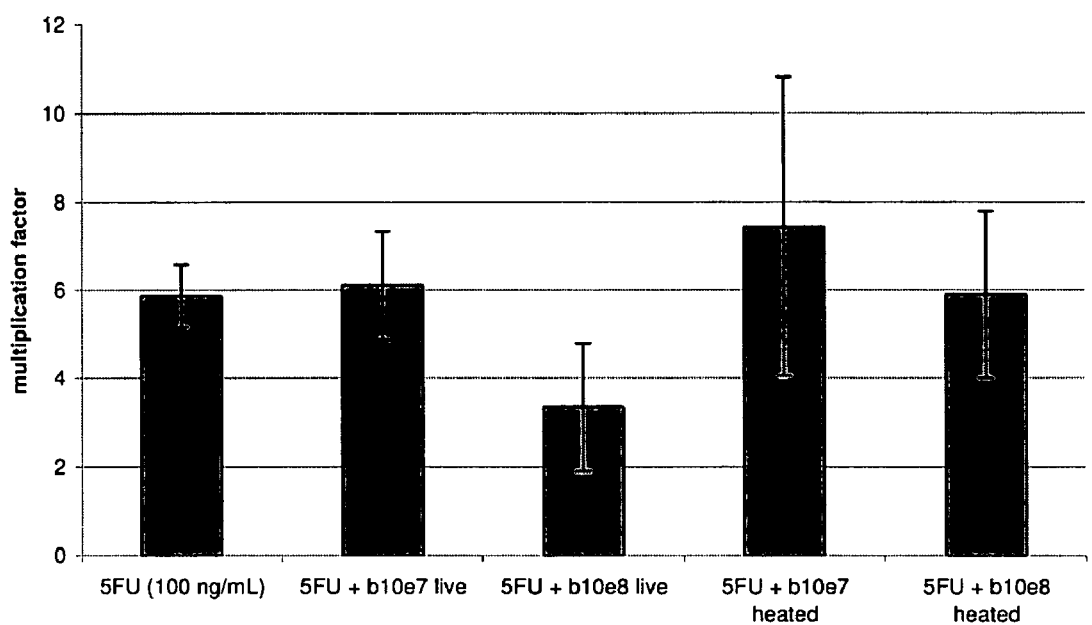
FIG. 21 is a graph showing the effect of the composition according to a preferred embodiment of the invention on Fas receptor expression.

FIG. 21 shows the effect of the composition according to a preferred embodiment on Fas receptor expression.

Figure 22:
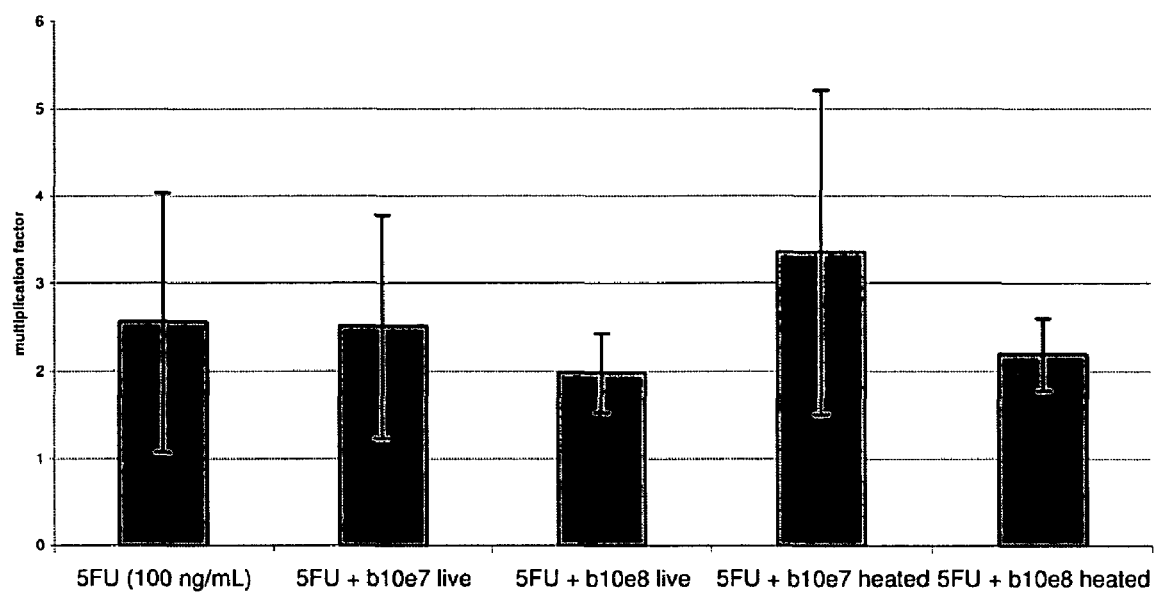
FIG. 22 is a graph showing the effect of the composition according to a preferred embodiment of the invention on Fas ligand expression.

FIG. 22 shows the effect of Fas ligand expression.

Figure 23:
FIG. 23 shows Western blots illustrating the effect of the composition according to a preferred embodiment of the invention on the expression of a protein involved in apoptosis, protein p53.
Figure 23:
Figure 23:

FIG. 23 illustrates the effect of the composition according to a preferred embodiment of the invention on p53 protein expression.

Figure 24:
FIG. 24 shows Western blots illustrating the effect of the composition according to a preferred embodiment of the invention on the expression of a protein involved in apoptosis, protein p21.
Figure 24:
Figure 24:

FIG. 24 illustrates the effect of the composition according to a preferred embodiment of the invention on p21 protein expression.

Figure 25:
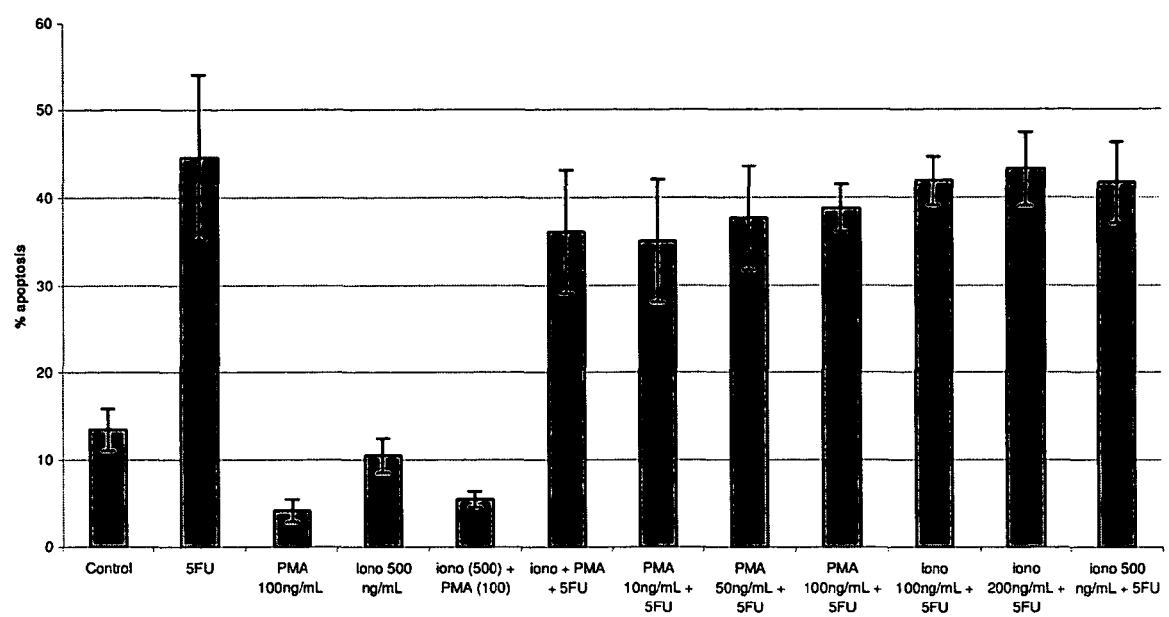
FIG. 25 is a graph showing the effect of PKC on apoptosis.

FIG. 25 illustrates the effect of PKC activation on apoptosis.

Figure 26:
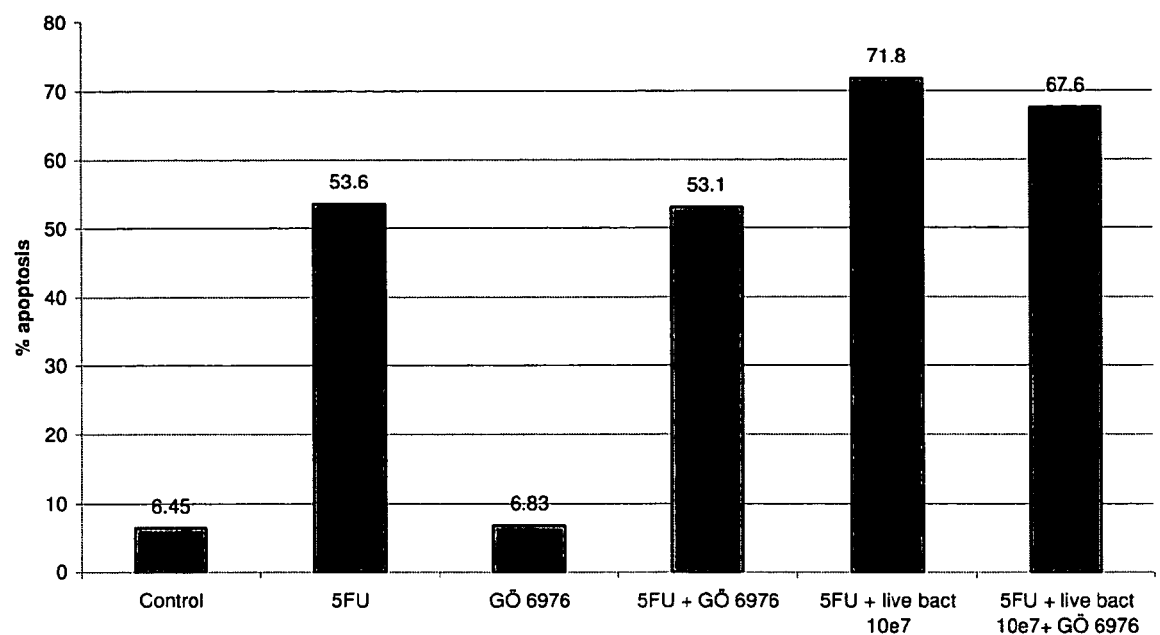
FIG. 26 is a graph showing the effect of the inhibition of PKC on apoptosis.

FIG. 26 illustrates the effect of PKC inhibition on apoptosis.

Figure 27:
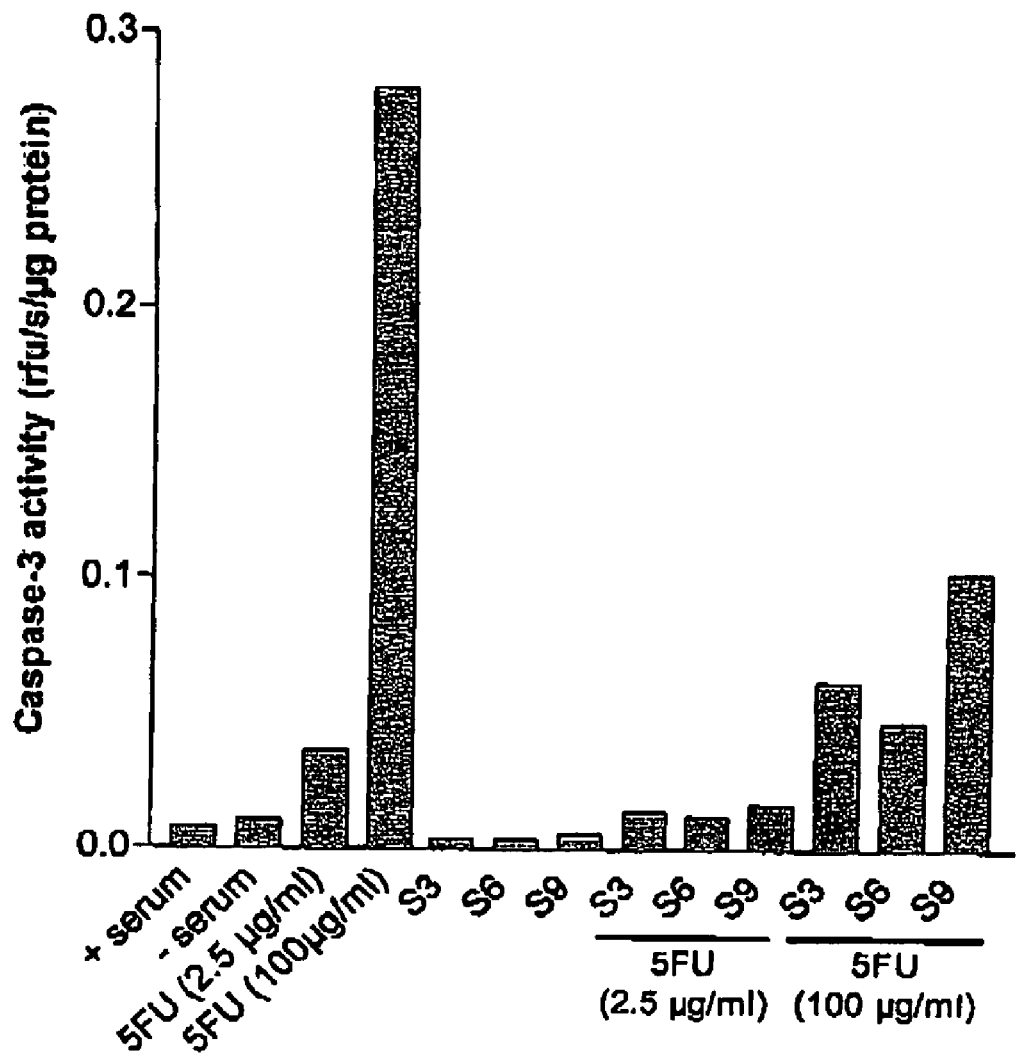
FIG. 27 is a graph illustrating the effect of supernatant of the lactic acid bacteria of the invention on the induction of caspase-3 activity in LS 513 cells.
Figure 28:
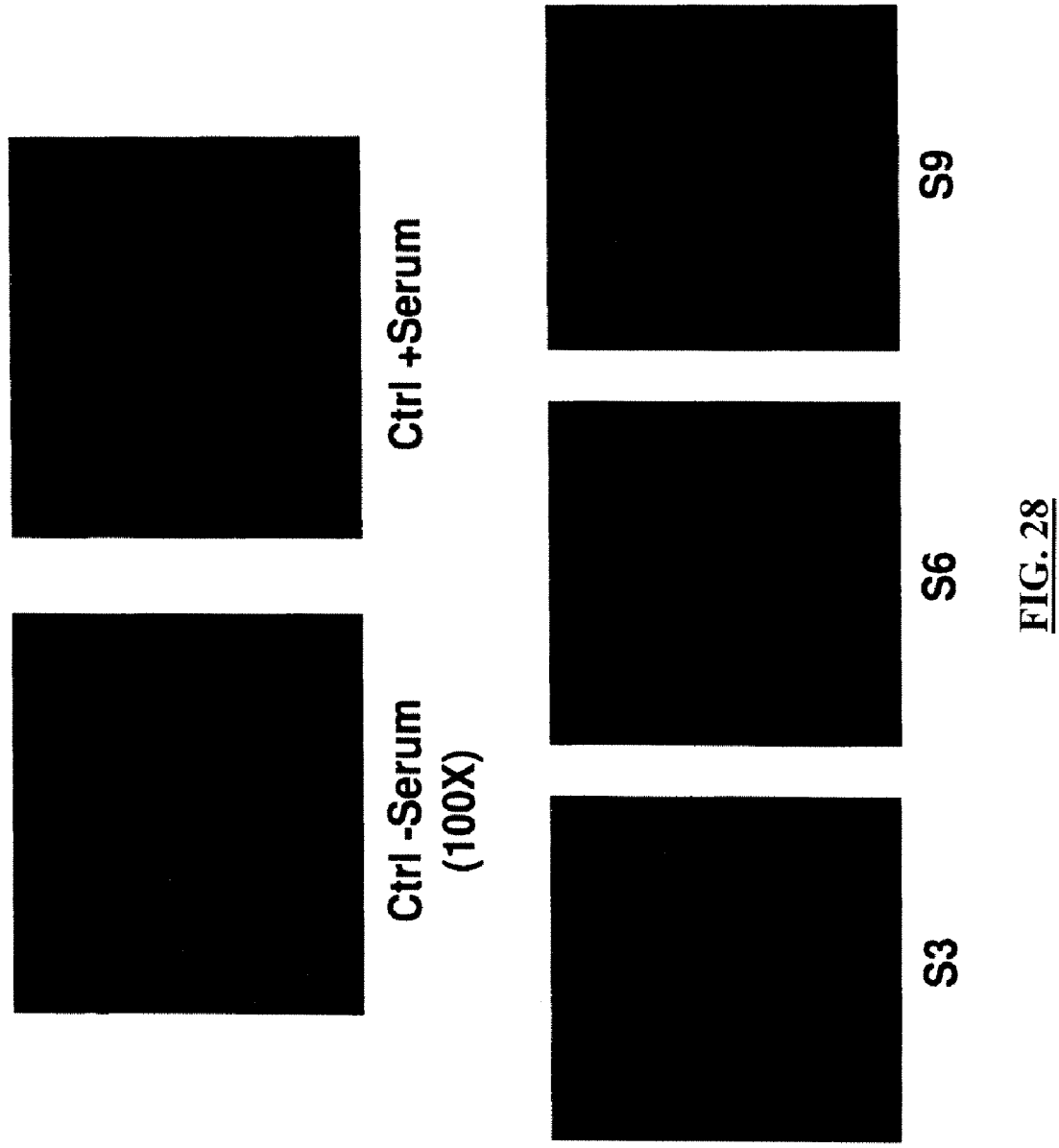
FIG. 28 shows photographs illustrating the effect the supernatant of the lactic acid bacteria of the invention on the coloration in fluorescence of the nucleus of LS 513 cells.
Figure 29:
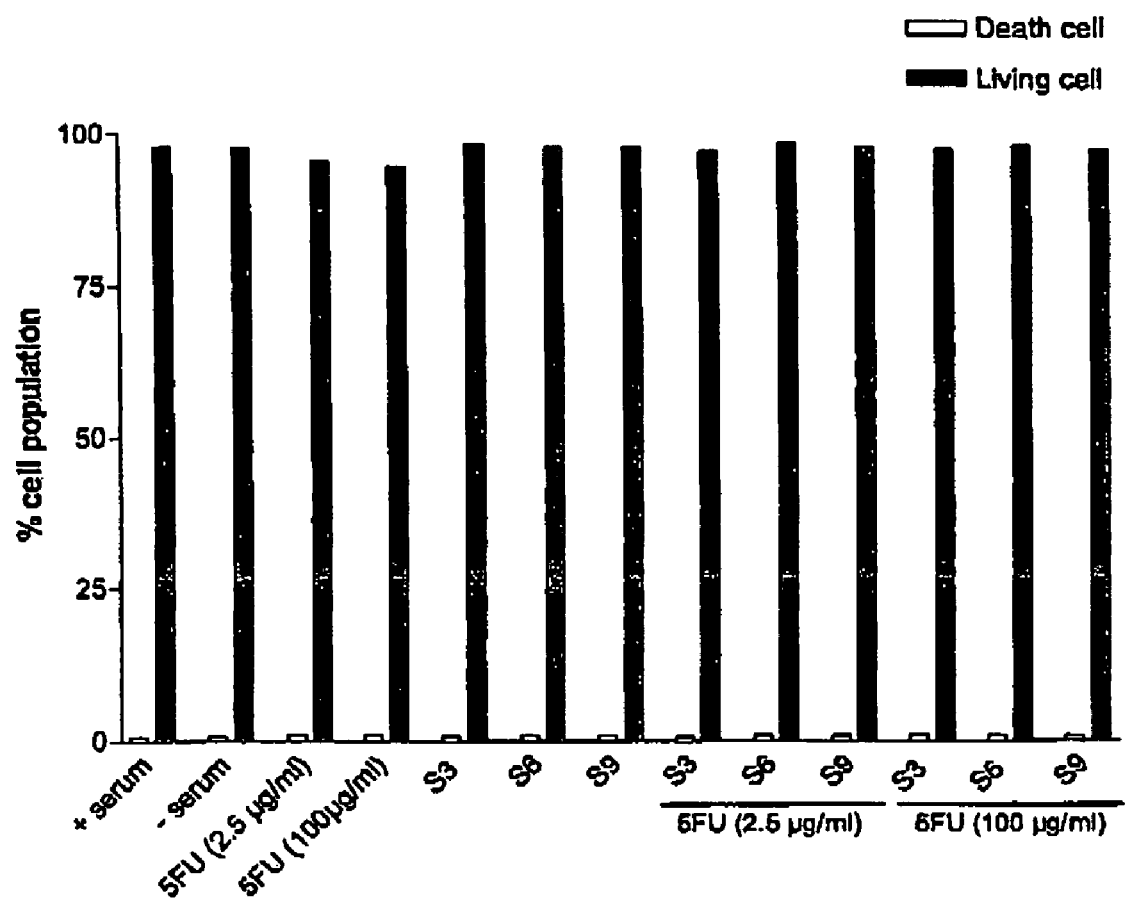
FIG. 29 is a graph illustrating the effect of the supernatant of the lactic acid bacteria of the invention on the viability of LS 513 cells.
Figure 30:
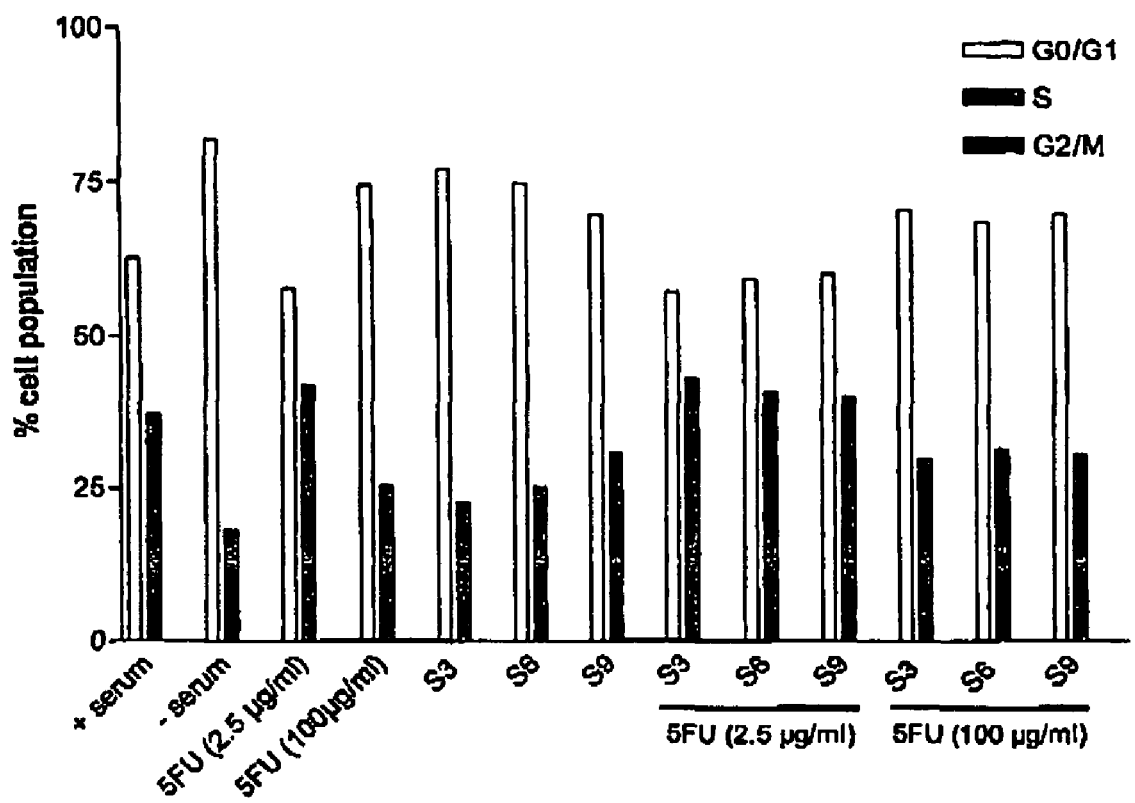
FIG. 30 is a graph illustrating the effect of the supernatant of the lactic acid bacteria of the inventions on the cellular gel of LS 513 cells.

6) Characterization of Lactic Acid Bacteria Supernatant of the Invention on the Apoptosis of LS 513 Intestinal Tumor Cells The apoptotic potential of bacterial supernatants on the LS 513 line, tumoral line was analysed. The results obtained on the activity of caspase-3 demonstrate that the supernatants, even in the presence of 5-fluorouracil (2.5 μg/mL and 100 μg/mL) do not activate this caspase in a significant way (FIG. 27). Instead, in the presence of 100 μg/mL of 5FU, the supernatants inhibit the activity of caspase-3. The fluorescent coloration of the nucleus of the cancer cells, with the help of the DAPI technique, did not allow to bring out nuclei where the chromatin is condensed, a fundamental characteristic of apoptotic cells. The coloration of nuclei is typical of healthy and live cells (FIG. 28, enlargement at 100× and 630×). In addition, the flow cytometry studies with the help of propidium iodide do not demonstrate cellular death (FIG. 29) nor significant disruption of the phases of the cellular cycle (FIG. 30). All of these results indicate that the bacterial supernatants do not induce apoptosis in the LS 513 cells.

Discussion

The action of intact bacteria, that is that are live and irradiated, on the cancer is the same. However, the non intact bacteria, for example the cells destroyed by the heat, seems to have an action contrary to the intact bacteria.

In addition, it has been noticed according to the work conducted in the context of the present invention that the efficacy of an anticancer agent such as 5FU is considerably increased in the presence of intact bacteria. This efficacy would be dose dependent. A more rapid apoptosis in the presence of live bacteria is noticed.

The presence of heated bacteria with 5FU would increase the expression of p21 protein. There could thus be modulation via an unknown apoptosis/cellular cycle (p21) regulator protein receptor. An increase of the p21 protein was noticed when there is less apoptosis and a decrease of the protein when there is more apoptosis.

Butyric acid is a product of live lactic acid bacteria and is present in the intestine. This product causes apoptosis in colon cancer cells in vitro. There will be a synergy between butyrate and 5FU on colon cancer. It has also been noticed that butyric acid inhibits the in vivo growth of human colon cancer on mice.

In view of what precedes, live lactic acid bacteria enter in synergy with 5FU to decrease the number of cancer cells in culture (MTT) or to increase apoptosis in the latter (flow cytometry).

The irradiated lactic acid bacteria have the same action as live bacteria whereas heated bacteria would have the opposite action. Hence, the intact form of lactic acid bacteria is necessary for their action against the tumoral cells. In addition, the action of bacteria is also dependent and proportional to the dose. The property to induce or to modulate apoptosis by the lactic acid bacteria of the invention was corroborated by the experiment demonstrating the non-apoptotic effect of the supernatant of said bacteria.

The expression of the caspase 3 as well as that of the p21 protein is modulated by live lactic acid bacteria in the same way as apoptosis.

*Lactobacillus acidophilus* (accession number I-1492) herein described was deposited on Nov. 15, 1994 at the Collection Nationale de Cultures de Microorganismes (CNCM; an International Depositary Authority, whose full post office address is Institut Pasteur, 28 Rue du Docteur Roux, F-75724, Paris, CEDEX 15, France) according to the provisions of the Budapest Treaty.

lactic acid bacteria strain and a pharmaceutically acceptable vehicle, said strain being *Lactobacillus acidophilus* I-1492 deposited at the CNCM.

8. The method according to claim 7, wherein said mammal is a human being.

9. The method of claim 7, wherein the bacterial strain is intact.

The invention claimed is:

1. A method to facilitate induction of apoptosis of a cancer cell in a mammal having cancer, the method comprising administering to the mammal *Lactobacillus acidophilus* I-1492 deposited at the CNCM.

2. The method of claim 1, wherein said *Lactobacillus acidophilus* I-1492 is intact.

3. The method of claim 1, further comprising administering to the mammal a strain of *Lactobacillus casei*.

4. The method of any one of claims 1, 2 or 3, further comprising administering an anticancer agent.

5. The method of claim 4, wherein the anticancer agent is 5 fluoro-uracil.

6. The method of claim 1, wherein said cancer cell is a colon cancer cell.

7. A method to facilitate apoptosis of cancer cells in a mammal having cancer, wherein the method comprises administering to said mammal a composition comprising a lactic acid bacteria strain and a pharmaceutically acceptable vehicle, said strain being *Lactobacillus acidophilus* I-1492 deposited at the CNCM.

10. The method of claim 7 or 9, wherein said composition further comprises a strain of *Lactobacillus casei*.

11. The method of claim 7 or 9, further comprising administering an anticancer agent.

12. The method of claim 11, wherein the anticancer agent is 5 fluoro-uracil.

13. The method of claim 2 or 9, wherein said intact *Lactobacillus acidophilus* I-1492 is in a live form.

14. The method of claim 2 or 9, wherein said intact *Lactobacillus acidophilus* I-1492 is irradiated.

15. A method to facilitate induction of apoptosis of a cancer cell, the method comprising contacting the cancer cell with *Lactobacillus acidophilus* I-1492 deposited at the CNCM.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial sequence
<220> FEATURE:
<223> OTHER INFORMATION: Other Information: Primer

<400> SEQUENCE: 1
cgaccccctg acccctgagt t                                                 21

<210> SEQ ID NO 2
<211> LENGTH: 22
<212> TYPE: DNA
<213> ORGANISM: Artificial sequence
<220> FEATURE:
<223> OTHER INFORMATION: Other Information: Primer

<400> SEQUENCE: 2
gccctcaagg tgttggagaa gt                                                22